United States Patent [19]

Mentrup et al.

[11] 4,215,119
[45] Jul. 29, 1980

[54] AMINOALKYL-SUBSTITUTED BENZIMIDAZOLIDIN-2-ONES

[75] Inventors: Anton Mentrup, Mainz-Kastel; Kurt Schromm, Ingelheim; Ernst-Otto Renth, Ingelheim; Richard Reichl, Ingelheim; Werner Traunecker, Münster-Sarmshein; Wolfgang Hoefke, Budenheim, all of Fed. Rep. of Germany

[73] Assignee: Boehringer Ingelheim GmbH, Ingelheim am Rhein, Fed. Rep. of Germany

[21] Appl. No.: 26,608

[22] Filed: Apr. 3, 1979

Related U.S. Application Data

[63] Continuation-in-part of Ser. No. 773,394, Mar. 2, 1977, Pat. No. 4,154,829.

[30] Foreign Application Priority Data

Mar. 9, 1976 [DE] Fed. Rep. of Germany ....... 2609645

[51] Int. Cl.² .............. A61K 31/535; A61K 31/415; C07D 235/26
[52] U.S. Cl. ..................... 424/248.5; 424/248.54; 424/258; 424/272; 424/273 B; 544/105; 546/158; 548/305; 548/221
[58] Field of Search .............. 548/305; 544/105; 546/158; 424/273 B, 272, 248.5, 248.54, 258; 260/307 C

[56] References Cited

U.S. PATENT DOCUMENTS

| | | | |
|---|---|---|---|
| 3,338,916 | 8/1967 | Hunziker | 548/305 |
| 4,154,829 | 5/1979 | Mentrup et al. | 544/105 |

FOREIGN PATENT DOCUMENTS

| | | | |
|---|---|---|---|
| 631296 | 11/1961 | Canada | 548/305 |
| 1516714 | 2/1968 | France | 548/320 |
| 995366 | 6/1965 | United Kingdom | 548/320 |

OTHER PUBLICATIONS

Davoll et al., Chem. Abst., 1960, vol. 54, cols. 9896–9898.
Bottu, Chem. Abst., 1970, vol. 72, No. 111,466n.
Seki et al., Chem. Abst., 1969, vol. 71, No. 61291h.

*Primary Examiner*—Natalie Trousof
*Attorney, Agent, or Firm*—Hammond & Littell, Weissenberger & Muserlian

[57] ABSTRACT

Racemic and optically active compounds of the formula $$Q-C_nH_{2n}-NH-R$$

wherein Q is where
- $R_1$ is hydrogen, halogen, alkyl of 1 to 4 carbon atoms, alkoxy of 1 to 4 carbon atoms, trifluoromethyl or amino,
- $R_2$ is hydrogen, halogen, alkyl of 1 to 4 carbon atoms, alkoxy of 1 to 4 carbon atoms or trifluoromethyl,
- $R_1$ and $R_2$, together with each other, are methylenedioxy or ethylenedioxy, and
- A is —O—, —CH$_2$—CH$_2$—, or —NR$_3$— where $R_3$ is hydrogen or alkyl or 1 to 4 carbon atoms,
- n is an integer from 2 to 6, inclusive, and
- R is hydrogen, benzyl or where
- $R_4$ is hydrogen, methyl or ethyl,
- $R_5$, $R_6$ and $R_7$, which may be identical to or different from each other, are each hydrogen, halogen, hydroxymethyl, trifluoromethyl, alkyl of 1 to 4 carbon atoms, alkoxy of 1 to 4 carbon atoms, nitro, cyano, —CONHR$_3$, —CONHOH, —COOR$_3$, R$_8$O—, methylsulfonylmethyl or, when one or two of R$_5$ through R$_7$ are other than halogen or trifluoromethyl, also —NR$_3$R$_9$, where
- $R_3$ has the meanings defined above,
- $R_8$ is hydrogen, alkanoyl of 1 to 20 carbon atoms, alkyl of 1 to 4 carbon atoms, or aralkyl, and
- $R_9$ is hydrogen, lower alkanoyl, methanesulfonyl, carbamoyl, dimethylsulfamoyl, or alkoxycarbonyl of 2 to 5 carbon atoms, and
- $R_5$ and $R_6$, together with each other, are —O—CH$_2$—O—, —O—CH$_2$—CH$_2$—O—, —CH=CH—CH=CH—, —O—CH$_2$—CONH—, —CH$_2$—CH$_2$—COHN— or —O—CO—NH—, and non-toxic, pharmacologically acceptable acid addition salts thereof. The compounds as well as their salts are useful as vasodilators and CNS-stimulators.

6 Claims, No Drawings

AMINOALKYL-SUBSTITUTED BENZIMIDAZOLIDIN-2-ONES

CROSS REFERENCE TO RELATED APPLICATION

This application is a continuation-in-part of copending U.S. patent application Ser. No. 773,394 filed Mar. 2, 1977, U.S. Pat. No. 4,154,829, incorporated herein by reference.

This invention relates to novel aminoalkyl-substituted heterocycles and non-toxic salts thereof, as well as to various methods of preparing these compounds.

More particularly, the present invention relates to a novel class of aminoalkyl-substituted heterocycles represented by the formula $$Q-C_nH_{2n}-NH-R \quad (I)$$

wherein Q is (IIa) (IIb)

where
 $R_1$ is hydrogen, halogen, alkyl of 1 to 4 carbon atoms, alkoxy of 1 to 4 carbon atoms, trifluoromethyl or amino,
 $R_2$ is hydrogen, halogen, alkyl of 1 to 4 carbon atoms, alkoxy of 1 to 4 carbon atoms or trifluoromethyl,
 $R_1$ and $R_2$, together with each other, are methylenedioxy or ethylenedioxy, and
 A is —O—, —CH$_2$—CH$_2$—, or —NR$_3$— where $R_3$ is hydrogen or alkyl of 1 to 4 carbon atoms,
 n is an integer from 2 to 6, inclusive, and
 R is hydrogen, benzyl or (III)

where
 $R_4$ is hydrogen, methyl or ethyl,
 $R_5$, $R_6$ and $R_7$, which may be identical to or different from each other, are each hydrogen, halogen, hydroxymethyl, trifluoromethyl, alkyl of 1 to 4 carbon atoms, alkoxy of 1 to 4 carbon atoms, nitro, cyano, -CONHR$_3$, —CONHOH, —COOR$_3$, $R_8$O—, methylsulfonylmethyl or, when one or two of $R_5$ through $R_7$ are other than halogen or trifluoromethyl, also —NR$_3$R$_9$, where
 $R_3$ has the meanings defined above,
 $R_8$ is hydrogen, alkanoyl of 1 to 20 carbon atoms, alkyl of 1 to 4 carbon atoms or aralkyl, and
 $R_9$ is hydrogen, lower alkanoyl, methanesulfonyl, carbamoyl, dimethylsulfamoyl, or alkoxycarbonyl of 2 to 5 carbon atoms, and
 $R_5$ and $R_6$, together with each other, are —O—CH$_2$—O, —O—CH$_2$—CH$_2$—O—, —CH=CH—CH=CH—, —O—CH$_2$—CONH—, —CH$_2$—CH$_2$—CONH— or —O—CO—NH—, and non-toxic, pharmacologically acceptable acid addition salts thereof.

The alkylene chain —C$_n$H$_{2n}$— in formula I may be straight or branched, and preferred embodiments thereof are —CH$_2$—CH$_2$—, —CH$_2$—CH$_2$—CH$_2$—, —CH$_2$—C(CH$_3$)$_2$— and primarily —CH$_2$—CH$_2$—C(CH$_3$)$_2$—, where the tertiary carbon atom is bonded to the nitrogen atom or the -NH-R moiety.

A subgenus thereunder is constituted by compounds of the formula I, wherein
 Q, A and $R_3$ have the meanings previously defined,
 $R_1$ is hydrogen, methoxy or amino,
 $R_2$ is hydrogen or methoxy,
 n is an integer from 3 to 6, inclusive,
 R is hydrogen or $R_5$ is hydrogen, —OR$_8$, —NHR$_9$, hydroxymethyl, cyano, —CONHR$_3$ or halogen.
 $R_6$ is hydrogen, hydroxyl or halogen,
 $R_7$ is hydrogen, chlorine, methyl or methoxy,
 $R_8$ is hydrogen, benzyl, methyl or alkanoyl, and
 $R_9$ is hydrogen, formyl, acetyl, methylsulfonyl, carbamoyl or dimethylsulfamoyl, provided that, when $R_6$ and/or $R_7$ are halogen, $R_5$ is other than —NHR$_9$; and non-toxic, pharmacologically acceptable acid addition salts thereof.

A particularly preferred subgenus thereunder is constituted by compounds of the formula I, wherein
 Q, A, $R_3$, $R_4$ and n have the meanings previously defined,
 $R_1$ is hydrogen, methoxy or amino,
 $R_2$ is hydrogen or methoxy,
 R is hydrogen or $R_5$ is hydrogen or hydroxyl,
 $R_6$ is hydrogen, hydroxyl, hydroxymethyl, cyano, —CONHR$_3$, —OR$_8$ or chlorine, $R_5$ and $R_6$, together with each other, are —CH=CH—CH=CH—, —OCH$_2$—CONH—, —CH$_2$—CH$_2$—CONH— or —O—CONH—, $R_7$ is hydrogen, methyl, methoxy, hydroxyl or chlorine, and $R_8$ is hydrogen, benzyl or lower alkanoyl, and non-toxic, pharmacologically acceptable acid addition salts thereof.

The compounds embraced by formula I may be prepared by the following methods, all of which involve known organic synthesis principles:

Method A

For the preparation of a compound of the formula I wherein R is a grouping of the formula III, by reacting an amine of the formula

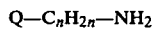

$$Q\text{—}C_nH_{2n}\text{—}NH_2 \qquad (IV)$$

wherein Q and n have the same meanings as in formula I, with a compound of the formula

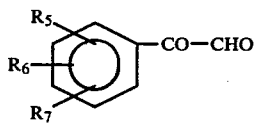

(Va)

or

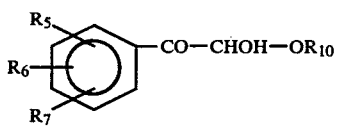

(Vb)

wherein $R_5$, $R_6$ and $R_7$ have the same meanings as in formula I, and $R_{10}$ is hydrogen or alkyl, under reductive amination conditions. Suitable reducing agents are complex hydrides, preferably sodium borohydride, or hydrogen in the presence of a hydrogenation catalyst, preferably platinum, palladium or nickel.

Method B

For the preparation of a compound of the formula I wherein R is a grouping of the formula III, by reducing a compound of the formula

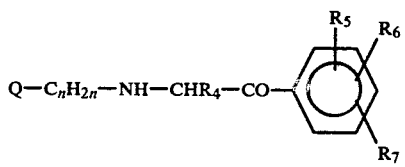

(VI)

wherein Q, n, $R_4$, $R_5$, $R_6$ and $R_7$ have the same meanings as in formula I, with a complex hydride, in particular sodium borohydride, or by catalytic hydrogenation with a conventional hydrogenation catalyst, for example, platinum, palladium or nickel.

Method C

For the preparation of a compound of the formula I, wherein R is a grouping of the formula III, by reacting an epoxide of the formula

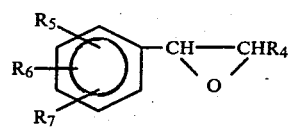

(VII)

wherein $R_4$, $R_5$, $R_6$ and $R_7$ have the same meanings as in formula I, with an amine of the formula IV; or by reacting a halohydrin of the formula

(VIII)

wherein $R_4$, $R_5$, $R_6$ and $R_7$ have the same meanings as in formula I, and Hal is halogen, with an amine of the formula IV in the presence of an acid binding agent, such as potassium carbonate, sodium carbonate or an excess of the amine IV. The halohydrin of the formula VIII converts into the corresponding epoxide VII under the reaction conditions.

Method D

For the preparation of a compound of the formula I wherein —$C_nH_{2n}$— is

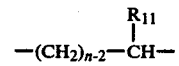

where n has the same meanings as in formula I, and $R_{11}$ is hydrogen or methyl, by reductive amination of a compound of the formula

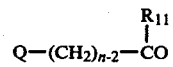

(IX)

wherein

Q and n have the same meanings as in formula I, and $R_{11}$ has the meanings defined above, with an amine of the formula

$$H_2N\text{-}R \qquad (X)$$

wherein R has the same meanings as in formula I. Suitable reducing agents are complex hydrides, such as sodium borohydride, or hydrogen in the presence of a catalyst, such as platinum, palladium or nickel; or by reducing a compound of the formula

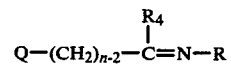

(XI)

wherein Q, n, $R_4$ and R have the meanings previously defined.

Method E

For the preparation of a compound of the formula I wherein R is a grouping of the formula III, by removing the -CH$_2$-aryl protective group from a compound of the formula

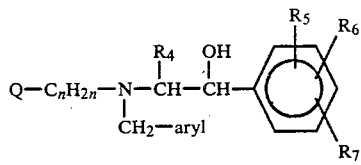

wherein Q, n, $R_4$, $R_5$, $R_6$ and $R_7$ have the same meanings as in formula I, by catalytic hydrogenation with a catalyst such as platinum, palladium or nickel.

Method F

For the preparation of a compound of the formula I in which at least one of substituents $R_5$, $R_6$ and $R_7$ is hydroxyl, by removing the arylmethyl protective group or groups from a corresponding compound wherein the respective hydroxyl substituent or substituents are arylmethylated. The removal of the arylmethyl group or groups is effected by catalytic hydrogenation with a catalyst such as platinum, palladium or nickel, or by ether cleavage with a hydrohalic acid or boron tribromide.

Method G

For the preparation of a compound of the formula I wherein $R_5$ is —NH-acyl or —NH—CO—$NH_2$, by reacting a compound of the formula

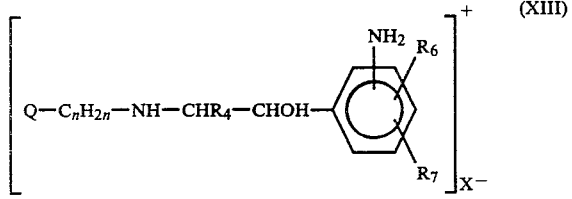

wherein

Q, n, $R_4$, $R_6$ and $R_7$ have the same meanings as in formula I, and

X is an anion, with a carboxylic acid anhydride for introduction of the acyl radical, or with a cyanate and an acid for introduction of the carbamoyl radical. At least one mol of an acid, which protects the secondary amino group by salt formation, is additionally required.

Method H

For the preparation of a compound of the formula I wherein $R_5$ is -$CONHR_3$, -$CONHNH_2$ or -CONHOH, by reacting an ester of the formula

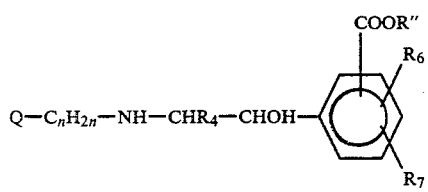

wherein

Q, n, $R_4$, $R_6$ and $R_7$ have the same meanings as in formula I, and

R" is alkyl or substituted alkyl, with a compound of the formula $$NH_2—R_{12} \quad (XV)$$

wherein $R_{12}$ is hydrogen, lower alkyl, hydroxyl or amino.

Method I

For the preparation of a compound of the formula I wherein R is hydrogen or benzyl, by removing the protective group or groups from a compound of the formula

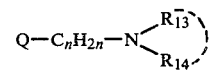

wherein

Q and n have the same meanings as in formula I, $R_{13}$ is arylmethyl, acyl or -$COOR_{15}$, $R_{14}$ is hydrogen or benzyl, and $R_{13}$ and $R_{14}$, together with each other, are a dicarboxylic acid radical, such as succinyl or phthalyl, or -$CHR_{15}$-, where $R_{15}$ is alkyl, arylmethyl or aryl.

When $R_{13}$ is acyl or -$COOR_{15}$, or $R_{13}$ and $R_{14}$ together are a dicarboxylic acid radical or -$CHR_{15}$-, the protective groups are removed by hydrolysis. When $R_{13}$ and $R_{14}$ together are a dicarboxylic acid radical, such as phthalyl, the removal may be effected by ring cleavage with hydrazine, followed by hydrolysis. When $R_{13}$ and/or $R_{14}$ are arylmethyl, the removal must be effected by hydrogenation in the presence of a catalyst, such as platinum, palladium or nickel. It is also possible to remove the protective group by catalytic hydrogenation when $R_{15}$ in -$COOR_{15}$ is arylmethyl.

Method J

For the preparation of a compound of the formula I wherein R is hydrogen, by reducing the nitro group in a compound of the formula

wherein Q and n have the same meanings as in formula I, preferably by catalytic hydrogenation with conventional catalysts, such as nickel.

The starting compounds for methods A through J are either known compounds or may be prepared by known methods.

In those instances where the end products of methods A through J are racemates, these may be separated into the optical antipode components by conventional methods.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, maleic acid, succinic acid, formic acid, p-amino-benzoic acid, methanesulfonic acid, 8-chloro-theophylline or the like.

The following examples illustrate the present invention and will enable others skilled in the art to understand it more completely. It should be understood, however, that the invention is not limited solely to the particular examples given below.

EXAMPLE I

A mixture consisting of 5.36 gm of 3,4-dichlorophenyl-glyoxal hydrate, 4.5 gm of 1-(3-amino-n-propyl)-1,2,3,4-tetrahydro-quinoline-(2) and 200 ml of ethanol was heated at 50° C. for 1 hour. Then, while cooling, it was admixed with 5 gm of sodium borohydride at 0° to 5° C., the mixture was stirred for 2 hours at room temperature and then acidified with hydrochloric acid, the ethanol was distilled off, and the residue was made alkaline with ammonia. 5.5 gm of the free base, m.p. 95° C., of the formula

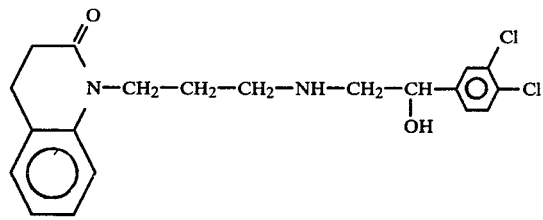

were obtained. Its hydrochloride, m.p. 185° C., was obtained by admixing the free base with the calculated amount of ethereal hydrochloric acid.

EXAMPLE 2

A mixture consisting of 11 gm of 1-(3,4-dibenzyloxyphenyl)-1-oxo-2-hydroxy-2-ethoxyethane (m.p. 114° C.), 5.6 gm of 1-(3,3-dimethyl-3-amino-n-propyl)-benzimidazolinone-(2) and 225 ml of ethanol was heated for 3 hours and subsequently admixed at 0° to 5° C. with 8 gm of sodium borohydride. The resulting solution was allowed to stand at room temperature for 12 hours, and then acidified with hydrochloric acid and worked up as described in the preceding example. 12.7 gm of free base, m.p. 130° C., of the formula

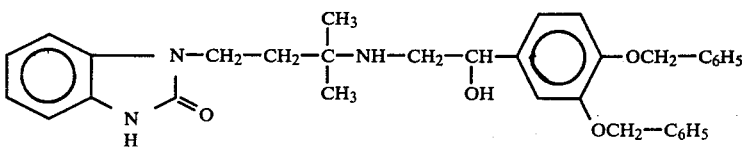

were obtained. Its maleate, m.p. 197° C., was obtained by adding a solution of maleic acid in acetonitrile to the base.

Using procedures and starting compounds analogous to those described in Examples 1 to 2, the compounds shown in the following table were also prepared. The indicated yields are in % of theory.

Table I

| Ex. No. | Formula | Yield % of theory | M.P. of Base °C. | Salt | m.p. of Salt °C. |
|---|---|---|---|---|---|
| 3 | C₆H₅CH₂—O—⟨⟩—CH(OH)—CH₂—NH—C(CH₃)₂—CH₂—CH₂—N⟨benzimidazolinone⟩ | 82 | 115 | | |
| 4 | HO—⟨⟩—CH(OH)—CH₂—NH—C(CH₃)₂—CH₂—CH₂—N⟨benzimidazolinone⟩ | 66 | | maleate | 134 |
| 5 | HN(SO₂CH₃)—⟨C₆H₅CH₂—O—⟩—CH(OH)—CH₂—NH—C(CH₃)₂—CH₂—CH₂—N⟨benzimidazolinone⟩ | 81 | | maleate | 217 |
| 6 | (C₆H₅CH₂O)₂—⟨⟩—CH(OH)—CH₂—NH—C(CH₃)₂—(CH₂)₃—N⟨benzimidazolinone⟩ | 78 | 151 | | |
| 7 | (C₆H₅CH₂O)₂—⟨⟩—CH(OH)—CH₂—NH—C(CH₃)₂—(CH₂)₃—N⟨benzimidazolinone⟩ | 79 | | succinate | 94 |
| 8 | Cl₂—⟨⟩—CH(OH)—CH₂—NH—C(CH₃)₂—CH₂—CH₂—N⟨benzoxazinone⟩ | 88 | | p-aminobenzoate | 166 |

Table I-continued

| Ex. No. | Formula | Yield % of theory | M.P. of Base °C. | Salt | m.p. of Salt °C. |
|---|---|---|---|---|---|
| 9 | C₆H₅—CH₂—O—[phenyl]—CH(OH)—CH₂—NH—(CH₂)₃—N[benzimidazolone-NH] ; C₆H₅CH₂O— | 60 | 93 | | |
| 10 | [naphthyl]—CH(OH)—CH₂—NH—CH₂—CH₂—N[benzimidazolone-NH] | 75 | 170 | methane-sulfonate | 185 |
| 11 | C₆H₅CH₂—O—[phenyl]—CH(OH)—CH₂—NH—C(CH₃)₂—(CH₂)₂—N[benzoxazinone]; C₆H₅CH₂—O— | 78 | amorphous | | |
| 12 | C₆H₅CH₂O—, CH₃, C₆H₅CH₂O—[phenyl]—CH(OH)—CH₂—NH—C(CH₃)₂—(CH₂)₂—N[benzimidazolone-NCH₃] | 74 | | hydro-chloride | 194 |
| 13 | C₆H₅CH₂O—, CH₃, C₆H₅CH₂O—[phenyl]—CH(OH)—CH₂—NH—C(CH₃)₂—(CH₂)₃—N[benzoxazinone] | 88 | | hydro-chloride | 215 |
| 14 | Cl, Cl—[phenyl]—CH(OH)—CH₂—NH—C(CH₃)₂—(CH₂)₂—N[benzimidazolone-NH] | 84 | | maleate | 209 |
| 15 | Cl, Cl—[phenyl]—CH(OH)—CH₂—NH—C(CH₃)₂—(CH₂)₂—N[benzimidazolone-NCH₃] | 66 | | succinate | 168 |
| 16 | C₆H₅CH₂O—[phenyl]—CH(OH)—CH₂—NH—C(CH₃)₂—(CH₂)₂—N[benzimidazolone-NCH₃]; C₆H₅CH₂O— | 66 | | sulfate | 250 |
| 17 | C₆H₅CH₂O—[phenyl]—CH(OH)—CH₂—NH—C(CH₃)₂—(CH₂)₂—N[benzimidazolone-NCH₃] | 88 | 135 | | |
| 18 | COOCH₃, HO—[phenyl]—CH(OH)—CH₂—NH—C(CH₃)₂—(CH₂)₂—N[—CO—N(phenyl)—CH₂CH₂—] | 66 | 126 | | |
| 19 | C₆H₅CH₂—O—[phenyl]—CH(OH)—CH₂—NH—C(CH₃)₂—(CH₂)₃—N[—CO—N(phenyl)—CH₂CH₂—]; C₆H₅CH₂O— | 69.5 | 134 | | |
| 20 | Cl—[phenyl]—CH(OH)—CH₂—NH—C(CH₃)₂—CH₂—CH₂—N[—CO—N(phenyl)—CH₂CH₂—] | 72 | | hydro-chloride | 252 |

Table I-continued

| Ex. No. | Formula | Yield % of theory | M.P. of Base °C. | Salt | m.p. of Salt °C. |
|---|---|---|---|---|---|
| 21 | C₆H₅CH₂—O—[Ar(NHSO₂CH₃)]—CH(OH)—CH₂—NH—C(CH₃)₂—(CH₂)₂—N(CO)N—(2-Cl-C₆H₄) | 87 | | sulfate | 225 |
| 22 | C₆H₅CH₂—O—[Ar(NHSO₂CH₃)]—CH(OH)—CH₂—NH—C(CH₃)₂—(CH₂)₂—N(CO)N—(2,6-Cl₂-C₆H₃) | 80 | | p-amino-benzoate | 123 |
| 23 | C₆H₅CH₂—O—[C₆H₄]—CH(OH)—CH₂—NH—C(CH₃)₂—(CH₂)₃—N(benzoxazin-3-one) | 68 | | sulfate | |
| 24 | C₆H₅CH₂—O—[C₆H₄]—CH(OH)—CH₂—NH—C(CH₃)₂—(CH₂)₂—N(imidazolidin-2-one)N—(3-CF₃-C₆H₄) | 82 | | hydro-chloride | 215 |
| 25 | (C₆H₅CH₂O)₂—[C₆H₃]—CH(OH)—CH₂—NH—(CH₂)₃—N(benzimidazolin-2-one, N-CH₃) | 93 | 93 | | |
| 26 | (C₆H₅CH₂O)₂—[C₆H₃]—CH(OH)—CH₂—NH—(CH₂)₃—N(benzoxazin-3-one) | 82 | | sulfate | 183 |
| 27 | C₆H₅CH₂O—[C₆H₄]—CH(OH)—CH₂—NH—(CH₂)₃—N(3,4-dihydroquinolin-2-one) | 80 | 68 | | |
| 28 | (C₆H₅CH₂O)₂—[C₆H₃]—CH(OH)—CH₂—NH—(CH₂)₃—N(3,4-dihydroquinolin-2-one) | 61 | | maleate | 137 |
| 29 | (C₆H₅CH₂O)₂—[C₆H₃]—CH(OH)—CH₂—NH—(CH₂)₃—N(3,4-dihydroquinolin-2-one) | 81 | | maleate | 123 |
| 30 | C₆H₅CH₂O—[Ar(NHSO₂CH₃)]—CH(OH)—CH₂—NH—C(CH₃)₂—CH₂—N(benzimidazolin-2-one)H | 70 | | hydro-chloride | 193 |

Table I-continued

| Ex. No. | Formula | Yield % of theory | M.P. of Base °C. | Salt | m.p. of Salt °C. |
|---|---|---|---|---|---|
| 31 | C₆H₅CH₂O—C₆H₃(NHSO₂CH₃)—CH(OH)—CH₂—NH—C(CH₃)₂—(CH₂)₂—N(benzimidazolin-2-one, N-CH₃) | 78 | | p-amino-benzoate | 118 |
| 32 | C₆H₅CH₂O—C₆H₃(NHSO₂CH₃)—CH(OH)—CH₂—NH—C(CH₃)₂—(CH₂)₂—N(benzoxazin-3-one) | 73 | 178 | maleate | 161 |
| 33 | C₆H₅CH₂O—C₆H₃(N(CH₃)SO₂CH₃)—CH(OH)—CH₂—NH—C(CH₃)₂—(CH₂)₂—N(benzimidazolin-2-one) | 62 | | succinate | 198 |
| 34 | C₆H₅CH₂O—C₆H₃(CH₃)—CH(OH)—CH₂—NH—C(CH₃)₂—(CH₂)₂—N(benzimidazolin-2-one) | 81 | 139 | succinate | 206 |
| 35 | C₆H₅CH₂O—C₆H₃(Cl)—CH(OH)—CH₂—NH—C(CH₃)₂—(CH₂)₂—N(benzimidazolin-2-one) | 75 | 141 | maleate | 218 |
| 36 | HO—C₆H₃(Cl)—CH(OH)—CH₂—NH—C(CH₃)₂—(CH₂)₂—N(benzimidazolin-2-one) | 69 | | maleate | 168 |
| 37 | C₆H₅CH₂O—C₆H₃(NHSO₂CH₃)—CH(OH)—CH₂—NH—(CH₂)₃—N(6,8-dichloro-3,4-dihydroquinolin-2(1H)-one) | 83 | | hydro-chloride | 196 |
| 38 | C₆H₅CH₂O—C₆H₃(N(C₃H₇)SO₂CH₃)—CH(OH)—CH₂—NH—C(CH₃)₂—(CH₂)₂—N(benzimidazolin-2-one) | 67 | | succinate | 180 |
| 39 | 2,5-(C₆H₅CH₂O)₂—C₆H₃—CH(OH)—CH₂—NH—C(CH₃)₂—(CH₂)₂—N(3,4-dihydroquinolin-2(1H)-one) | 84 | | maleate | 170 |
| 40 | HO—C₆H₃(COOCH₃)—CH(OH)—CH₂—NH—C(CH₃)₂—(CH₂)₂—N(3,4-dihydroquinolin-2(1H)-one) | 69 | | hydro-chloride | 170 |

Table I-continued

| Ex. No. | Formula | Yield % of theory | M.P. of Base °C. | Salt | m.p. of Salt °C. |
|---|---|---|---|---|---|
| 41 | C₆H₅CH₂O-[phenyl with HN-SO₂CH₃]-CH(OH)-CH₂-NH-C(CH₃)₂-(CH₂)₂-N[3,4-dihydroquinolin-2(1H)-one] | 79 | | hydro-chloride | 116 |
| 42 | [2-Cl-phenyl]-CH(OH)-CH₂-NH-C(CH₃)₂-(CH₂)₂-N[benzimidazol-2(3H)-one] | 70 | | maleate | 210 |
| 43 | [2-Cl-phenyl]-CH(OH)-CH₂-NH-C(CH₃)₂-(CH₂)₃-N[benzimidazol-2(3H)-one] | 68 | | hydro-chloride | 239 |
| 44 | [2-Cl-phenyl]-CH(OH)-CH₂-NH-C(CH₃)₂-(CH₂)₂-N[3,4-dihydroquinolin-2(1H)-one] | 50 | | p-amino-benzoate | 152,5 |
| 45 | [2-Cl-phenyl]-CH(OH)-CH₂-NH-C(CH₃)₂-(CH₂)₂-N[benzoxazin-3-one] | 53 | | p-amino-benzoate | 159 |
| 46 | [3-NO₂-phenyl]-CH(OH)-CH₂-NH-C(CH₃)₂-(CH₂)₂-N[benzimidazol-2(3H)-one] | 38 | 163 | hydro-chloride | 148 |
| 47 | [3,4-di(C₆H₅CH₂O)-2-CH₃-phenyl]-CH(OH)-CH₂-NH-C(CH₃)₂-(CH₂)₃-N[benzimidazol-2(3H)-one] | 86 | | hydro-chloride | 183 |
| 48 | [3,5-di(C₆H₅CH₂O)-phenyl]-CH(OH)-CH₂-NH-C(CH₃)₂-CH₂-CH₂-N[imidazolidin-2-one-3-phenyl] | 88.5 | 116 | | |
| 49 | [C₆H₅CH₂O-phenyl]-CH(OH)-CH₂-NH-C(CH₃)₂-CH₂-CH₂-N[imidazolidin-2-one-3-phenyl] | 95.4 | 122 | | |
| 50 | [C₆H₅CH₂O-, N(CH₃)SO₂CH₃-phenyl]-CH(OH)-CH₂-NH-C(CH₃)₂-CH₂-CH₂-N[imidazolidin-2-one-3-phenyl] | 84,5 | | hydro-chloride | 197 |
| 51 | [C₆H₅CH₂-O-, N(CH₃)SO₂CH₃-phenyl]-CH(OH)-CH₂-NH-(CH₂)₃-N[imidazolidin-2-one-3-phenyl] | 86 | | hydro-chloride | 142 |

Table I-continued

| Ex. No. | Formula | Yield % of theory | M.P. of Base °C. | Salt | m.p. of Salt °C. |
|---|---|---|---|---|---|
| 52 | [structure: C₆H₅—CH₂—O—(phenyl with NSO₂CH₃/C₃H₇)—CH(OH)—CH₂—NH—C(CH₃)₂—(CH₂)₂—N(CO)N—C₆H₅ (imidazolidinone)] | 83 | | hydro-chloride | 176 |
| 53 | [structure: C₆H₅CH₂O, OCH₃, C₆H₅CH₂—O—(phenyl)—CH(OH)—CH₂—NH—C(CH₃)₂—(CH₂)₂—N(CO)N—C₆H₅] | 77 | 107 | | |
| 54 | [structure: methylenedioxyphenyl—CH(OH)—CH₂—NH—C(CH₃)₂—CH₂—CH₂—N(imidazolidinone)—C₆H₅] | 64 | | hydro-chloride | 233 |
| 55 | [structure: methylenedioxyphenyl—CH(OH)—CH₂—NH—C(CH₃)₂—CH₂—CH₂—N(benzimidazolinone-NH)] | 75 | | maleate | 218 |
| 56 | [structure: 3-Cl-phenyl-N(imidazolidinone)N—CH₂—CH₂—C(CH₃)₂—NH—CH₂—CH(OH)—(phenyl with O—CH₂C₆H₅ and NH—SO₂CH₃)] | 70.3 | | hydro-chloride | 196 |
| 57 | [structure: 3,4-dimethoxyphenyl-N(imidazolidinone)N—CH₂—CH₂—C(CH₃)₂—NH—CH₂—CH(OH)—(phenyl with O—CH₂C₆H₅ and NH—SO₂CH₃)] | 70.3 | | hydro-chloride | 181 |
| 58 | [structure: 4-CH₃O-phenyl-N(imidazolidinone)N—CH₂—CH₂—C(CH₃)₂—NH—CH₂—CH(OH)—(phenyl with O—CH₂C₆H₅ and NH—SO₂CH₃)] | 62 | | sulfate | 259 |
| 59 | [structure: dihydroquinolin-2-one—N—CH₂—CH₂—C(CH₃)₂—NH—CH₂—CH(OH)—naphthyl] | 89 | 122 | hydro-chloride | 172 |
| 60 | [structure: benzimidazolinone—CH₂—CH₂—C(CH₃)₂—NH—CH₂—CH(OH)—naphthyl] | 87 | 108 | maleate | 242 |
| 61 | [structure: 1-methylbenzimidazole—CH₂—CH₂—C(CH₃)₂—NH—CH₂—CH(OH)—naphthyl] | 83 | 127 | hydro-chloride | 220 |

Table I-continued

| Ex. No. | Formula | Yield % of theory | M.P. of Base °C. | Salt | m.p. of Salt °C. |
|---|---|---|---|---|---|
| 62 | (3-oxo-benzoxazine)-N-CH₂-CH₂-C(CH₃)₂-NH-CH₂-CH(OH)-naphthyl | 88 | 137 | methane-sulfonate | 170 |
| 63 | (1-methyl-benzimidazol-2-one)-N-CH₂-CH₂-C(CH₃)₂-NH-CH₂-CH(OH)-(methylenedioxyphenyl) | 79 | 183 | hydro-chloride | 198 |
| 64 | (3-oxo-benzoxazine)-N-CH₂-CH₂-C(CH₃)₂-NH-CH₂-CH(OH)-(methylenedioxyphenyl) | 68 | 116 | sulfate | 248 |
| 65 | (3-oxo-tetrahydroquinoline)-N-CH₂-CH₂-C(CH₃)₂-NH-CH₂-CH(OH)-(methylenedioxyphenyl) | 86 | | Formate | 143 |
| 66 | (benzimidazol-2-one)-N-CH₂-CH₂-C(CH₃)₂-NH-CH₂-CH(OH)-(2-OCH₂C₆H₅-5-CN-phenyl) | 78 | 112-114 | hydro-chloride . H₂O | 227-228 |
| 67 | (benzimidazol-2-one)-N-CH₂-CH₂-C(CH₃)₂-NH-CH₂-CH(OH)-(2-OCH₂C₆H₅-3-CH₂OH-phenyl) | 71 | 84 | | |
| 68 | (benzoxazol-2-one)-N-CH₂-CH₂-C(CH₃)₂-NH-CH₂-CH(OH)-naphthyl | 73 | | hydro-chloride | 197 |
| 69 | (benzoxazol-2-one)-N-CH₂-CH₂-C(CH₃)₂-NH-CH₂-CH(OH)-(2-OCH₂C₆H₅-3-CH₂OCH₂C₆H₅-phenyl) | 79 | 168 | maleate | 88 |
| 70 | (benzoxazol-2-one)-N-CH₂-CH₂-C(CH₃)₂-NH-CH₂-CH(OH)-(methylenedioxyphenyl) | 73 | | hydro-chloride | 187 |
| 71 | (benzimidazol-2-one)-N-CH₂-CH₂-C(CH₃)₂-NH-CH₂-CH(OH)-(OCH₂C₆H₅, oxazinone-fused)phenyl | 69 | | hydro-chloride | decomp. >200° |
| 72 | (benzimidazol-2-one)-N-CH₂-CH₂-CH₂-NH-CH₂-CH(OH)-(OCH₂C₆H₅, oxazinone-fused)phenyl | | | | |

Table I-continued

| Ex. No. | Formula | Yield % of theory | M.P. of Base °C. | Salt | m.p. of Salt °C. |
|---|---|---|---|---|---|
| 73 | | | | | |
| 74 | | | | | |
| 75 | | | | | |
| 76 | | | | | |
| 77 | | | | | |
| 78 | | | | | |

Table I-continued

| Ex. No. | Formula | Yield % of theory | M.P. of Base °C. | Salt | m.p. of Salt °C. |
|---|---|---|---|---|---|
| 79 | | | | | |
| 80 | | | | | |
| 81 | | | | | |
| 82 | | | | | |
| 83 | | | | | |

EXAMPLE 84

A mixture consisting of 42.5 gm of 3,4-dibenzyloxyphenyl-ω-bromoacetophenone, 29 gm of N-methyl-N'-(2-benzylamino-ethyl)-benzimidazolinone-(2), 25 gm of sodium carbonate and 600 ml of acetonitrile was refluxed for 2 hours. Thereafter, the precipitated inorganic products were filtered off, and the solvent was distilled out of the filtrate under a water aspirator vacuum in a rotary evaporator, the residue was taken up in 900 ml of methanol, 30 ml of an ethereal 12% hydrochloric acid solution and 15 ml of an ethereal 1% palladium chloride solution were added, and the mixture was hydrogenated in the presence of 2 gm of activated charcoal at 60° C. and 6 atmospheres until 3 molar equivalents of hydrogen had been absorbed. After separation of the catalyst, about half of the methanol was distilled off, and the residual solution was admixed with 500 ml of acetonitrile. 32 gm of 1-(3,4-dihydroxyphenyl)-1-oxo-2-[(3-methyl)-benzimidazolinone-(2)-yl]-ethylaminoethane hydrochloride crystallized out which, after recrystallization from water, had a melting point of 250° C. 8 gm of this aminoketone were hydrogenated in 400 ml of methanol in the presence of 1 gm of platinum oxide under standard conditions until 1 molar equivalent of hydrogen had been absorbed, and the hydrogenation product was isolated as its hydrochloride of the formula

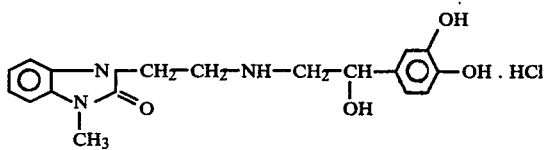

having a melting point of 185° C. The yield was 88% of theory.

Using an analogous procedure and corresponding starting compounds, the compounds shown in the following table were also prepared:

TABLE II
| Ex. No. | Formula | Yield % of theory | m.p. of Base °C. | Salt | m.p. of Salt °C. |
|---|---|---|---|---|---|
| 85 | 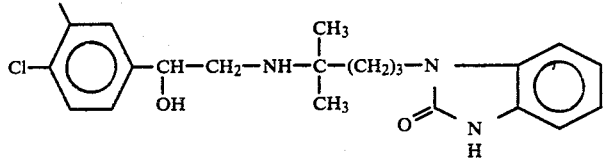 | 89 | | p-amino-benzoate | 161 |
| 86 | 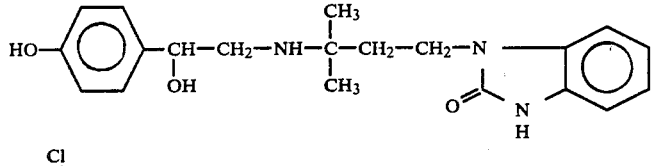 | 92 | | maleate | 134 |
| 87 | 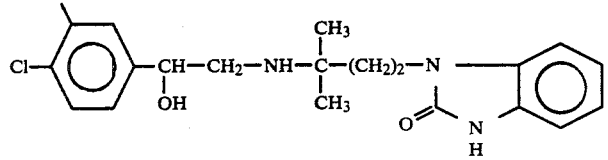 | 92 | | maleate | 209 |
| 88 | 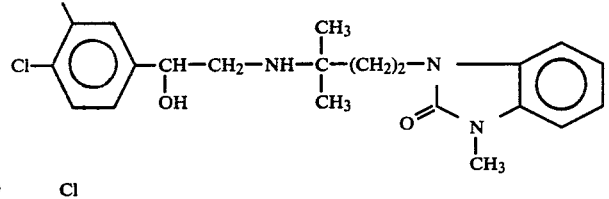 | 93 | | succinate | 168 |
| 89 | 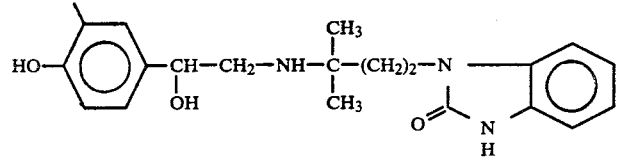 | 90 | | maleate | 168 |
| 90 | 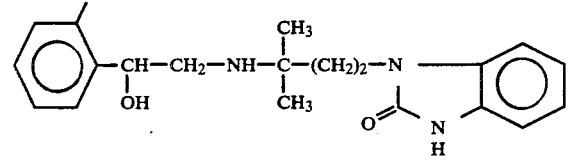 | 96 | | maleate | 210 |
| 91 | 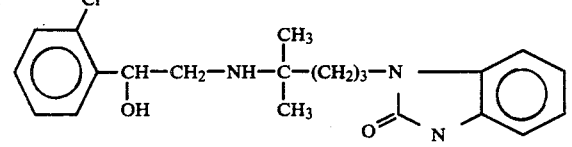 | 93 | | hydro-chloride | 239 |
| 92 | 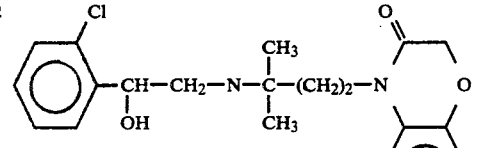 | 94 | | p-amino-benzoate | 159 |
| 93 | 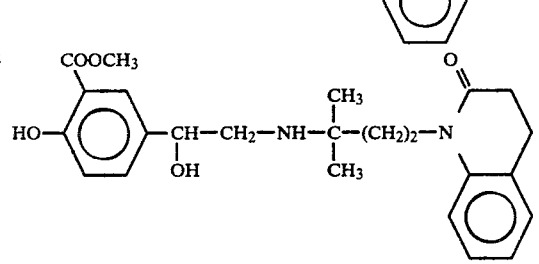 | 88 | | hydro-chloride | 170 |

TABLE II-continued

| Ex. No. | Formula | Yield % of theory | m.p. of Base °C. | Salt | m.p. of Salt °C. |
|---|---|---|---|---|---|
| 94 | (HO)(HO)C₆H₃–CH(OH)–CH₂–NH–CH₂–CH₂–CH₂–N(benzimidazolinone) | 89 | | succinate | 204 |
| 95 | (HO)(HO)C₆H₃–CH(OH)–CH₂–NH–CH₂–CH₂–N(benzimidazolinone) | 78 | | cyclamate | 176 |
| 96 | (2-naphthyl)–CH(OH)–CH₂–NH–CH₂–CH₂–N(benzimidazolinone) | 93 | 170 | methane-sulfonate | 185 |
| 97 | (HO)(HO)C₆H₃–CH(OH)–CH₂–NH–C(CH₃)₂–CH₂–CH₂–N(benzimidazolinone) | 90 | | maleate | 138 |
| 98 | (HO)(HO)C₆H₃–CH(OH)–CH₂–NH–C(CH₃)₂–CH₂–CH₂–N(benzimidazolinone) | 94 | | maleate H₂O | 180 |
| 99 | (HO)(HO)(CH₃)C₆H₂–CH(OH)–CH₂–NH–C(CH₃)₂–CH₂–CH₂–N(benzimidazolinone) | 85 | | maleate | 157 |
| 100 | (HO)C₆H₄–CH(OH)–CH₂–NH–C(CH₃)₂–CH₂–CH₂–N(benzimidazolinone) | 92 | | maleate | 180 |
| 101 | (HO)(HO)C₆H₃–CH(OH)–CH₂–NH–C(CH₃)₂–CH₂–N(benzimidazolinone) | 90 | | hydrochloride · 2 H₂O | 275 |
| 102 | (HO)C₆H₄–CH(OH)–CH₂–NH–C(CH₃)₂–CH₂–N(benzimidazolinone) | 94 | | hydrochloride | 265 |

TABLE II-continued
| Ex. No. | Formula | Yield % of theory | m.p. of Base °C. | Salt | m.p. of Salt °C. |
|---|---|---|---|---|---|
| 103 | 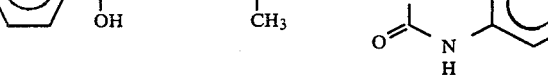 | 93 | | hydro-chloride | 177 |
| 104 | 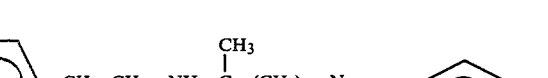 | 89 | | succinate | 215 |
| 105 | 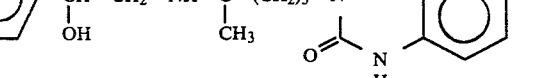 | 92 | | succinate . H₂O | 128 |
| 106 | 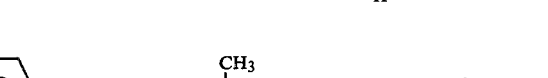 | 94 | | p-amino-benzoate | 166 |
| 107 | 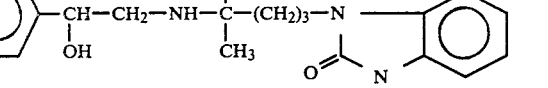 | 91 | | succinate | 169–71 |
| 108 | 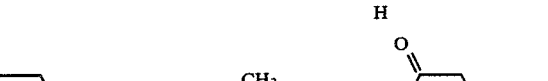 | 90 | | p-amino-benzoate | 193 |
| 109 | 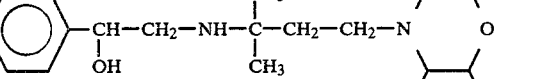 | 84 | | succinate | 176 |
| 110 |  | 90 | 212 | p-amino-benzoate | 234 |

TABLE II-continued

| Ex. No. | Formula | Yield % of theory | m.p. of Base °C. | Salt | m.p. of Salt °C. |
|---|---|---|---|---|---|
| 111 | HO-C6H4-CH(OH)-CH2-NH-C(CH3)2-CH2-CH2-N(benzimidazolinone-N-CH3) | 92 | 148 | p-amino-benzoate | 191 |
| 112 | (HO)2-C6H3-CH(OH)-CH2-NH-(CH2)3-N(benzimidazolinone-N-CH3) | 90 | | hydro-chloride | 190 |
| 113 | (HO)2-C6H3-CH(OH)-CH2-NH-(CH2)3-N(benzoxazinone) | 89 | | succinate | 189 |
| 114 | HO,CH3,HO-C6H2-CH(OH)-CH2-NH-C(CH3)2-CH2-CH2-N(benzoxazinone) | 90 | | Formiate · ½ CH3CN | 159 |
| 115 | Cl2-C6H3-CH(OH)-CH2-NH-(CH2)3-N(dihydroquinolinone) | 93 | 95 | hydro-chloride | 185 |
| 116 | HO-C6H4-CH(OH)-CH2-NH-(CH2)3-N(dihydroquinolinone) | 94 | | hydro-chloride | 198 |
| 117 | (HO)2-C6H3-CH(OH)-CH2-NH-(CH2)3-N(dihydroquinolinone) | 93 | | p-amino-benzoate | 199 |
| 118 | (HO)2-C6H3-CH(OH)-CH2-NH-(CH2)3-N(dihydroquinolinone) | 90 | | hydro-chloride | 175 |

TABLE II-continued

| Ex. No. | Formula | Yield % of theory | m.p. of Base °C. | Salt | m.p. of Salt °C. |
|---|---|---|---|---|---|
| 119 | HO-C₆H₃(HNSO₂CH₃)-CH(OH)-CH₂-NH-C(CH₃)₂-CH₂-N(benzimidazolinone) | 91 | 206 | hydrochloride | 169 |
| 120 | HO-C₆H₃(HNSO₂CH₃)-CH(OH)-CH₂-NH-C(CH₃)₂-CH₂-CH₂-N(N-methylbenzimidazolinone) | 94 | 200 | hydrochloride | 201 |
| 121 | HO-C₆H₃(HNSO₂CH₃)-CH(OH)-CH₂-NH-C(CH₃)₂-CH₂-CH₂-N(benzoxazinone) | 85 | 198 | hydrochloride | 157 |
| 122 | C₆H₅CH₂-O-C₆H₃(N(CH₃)SO₂CH₃)-CH(OH)-CH₂-NH-C(CH₃)₂-(CH₂)₂-N(benzimidazolinone) | 92 | — | succinate | 198 |
| 123 | HO-C₆H₃(N(CH₃)SO₂CH₃)-CH(OH)-CH₂-NH-C(CH₃)₂-(CH₂)₂-N(benzimidazolinone) | 89 | — | acid maleate | 202 |
| 124 | HO-C₆H₃(CH₃)-CH(OH)-CH₂-NH-C(CH₃)₂-CH₂-CH₂-N(benzimidazolinone) | 97 | — | acid maleate | 180 |
| 125 | HO-C₆H₂(Cl)-CH(OH)-CH₂-NH-C(CH₃)₂-CH₂-CH₂-N(benzimidazolinone) | 92 | — | acid maleate | 168 |
| 126 | HO-C₆H₃(NHSO₂CH₃)-CH(OH)-CH₂-NH-(CH₂)₃-N(6,8-dichloro-3,4-dihydroquinolin-2(1H)-one) | 89 | — | hydrochloride | 230 |

TABLE II-continued

| Ex. No. | Formula | Yield % of theory | m.p. of Base °C. | Salt | m.p. of Salt °C. |
|---|---|---|---|---|---|
| 127 | HO–C₆H₃(CONH₂)–CH(OH)–CH₂–NH–C(CH₃)₂–CH₂–CH₂–N(benzimidazolinone) | 94 | | hydrochloride | 252 |
| 128 | HO–C₆H₃(N(CH₃)SO₂CH₃)–CH(OH)–CH₂–NH–(CH₂)₃–N(3-oxo-benzoxazine) | 90 | | succinate | 173 |
| 129 | HO–C₆H₃(CONH₂)–CH(OH)–CH₂–NH–C(CH₃)₂–(CH₂)₂–N(3-oxo-benzoxazine) | 91 | 198 | hydrochloride | 235 |
| 130 | HO–C₆H₃(N(CH₃)SO₂CH₃)–CH(OH)–CH₂–NH–C(CH₃)₂–CH₂–CH₂–N(3-oxo-benzoxazine) | 84 | | succinate | 212 |
| 131 | HO–C₆H₃(N(C₃H₇)SO₂CH₃)–CH(OH)–CH₂–NH–C(CH₃)₂–CH₂–CH₂–N(benzimidazolinone) | 89 | | succinate | 218 |
| 132 | HO–C₆H₃(CONHCH₃)–CH(OH)–CH₂–NH–C(CH₃)₂–(CH₂)₂–N(3-oxo-benzoxazine) | 94 | 180 | hydrochloride | 190 |
| 133 | 3,5-(HO)₂–C₆H₃–CH(OH)–CH₂–NH–C(CH₃)₂–(CH₂)₂–N(2-oxo-tetrahydroquinoline) | 88 | | formate | 214 |

TABLE II-continued
| Ex. No. | Formula | Yield % of theory | m.p. of Base °C. | Salt | m.p. of Salt °C. |
|---|---|---|---|---|---|
| 134 | 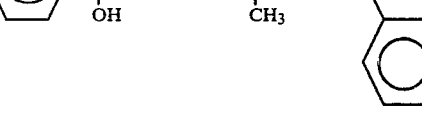 | 92 | 190 | hydro-chloride | 225 |
| 135 | 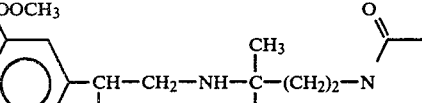 | 87 | | hydro-chloride | 170 |
| 136 | 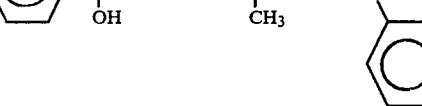 | 90 | 193 | hydro-chloride | 196 |
| 137 | 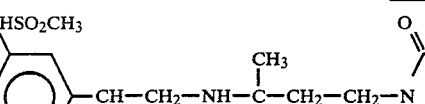 | 96 | | maleate | 210 |
| 138 | 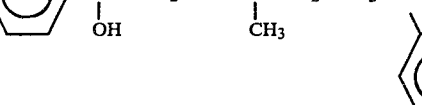 | 96 | | hydro-chloride | 239 |
| 139 | 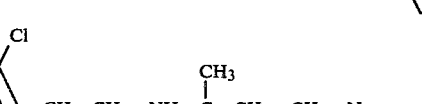 | 93 | | p-amino-benzoate | 152.5 |
| 140 | 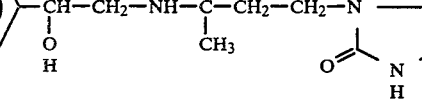 | 90 | | p-amino-benzoate | 159 |
| 141 | 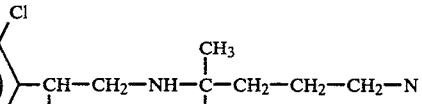 | 67 | 163 | hydro-chloride | 148 |

TABLE II-continued

| Ex. No. | Formula | Yield % of theory | m.p. of Base °C. | Salt | m.p. of Salt °C. |
|---|---|---|---|---|---|
| 142 | HO—, CH₃, HO—, OH —CH(OH)—CH₂—NH—C(CH₃)₂—(CH₂)₃—N(benzimidazolone) | 81 | | p-amino-benzoate | 190 |
| 143 | NH₂—Ph—CH(OH)—CH₂—NH—C(CH₃)₂—(CH₂)₃—N(benzimidazolone) | 79 | | hydro-chloride | 262 |
| 144 | NHCOCH₃—Ph—CH(OH)—CH₂—NH—C(CH₃)₂—CH₂—CH₂—N(benzimidazolone) | 84 | | maleate | 202 |
| 145 | NHCONH₂—Ph—CH(OH)—CH₂—NH—C(CH₃)₂—(CH₂)₃—N(benzimidazolone) | 88 | | maleate | 202 |
| 146 | HO, HO—Ph—CH(OH)—CH₂—NH—C(CH₃)₂—(CH₂)₂—N(oxazolidinone-N-phenyl) | 85 | 180 | succinate | 203 |
| 147 | HO—Ph—CH(OH)—CH₂—NH—C(CH₃)₂—CH₂—CH₂—N(oxazolidinone-N-phenyl) | 88 | | p-amino-benzoate | 196 |
| 148 | NHSO₂CH₃, HO—Ph—CH(OH)—CH₂—NH—C(CH₃)₂—CH₂—CH₂—N(oxazolidinone-N-phenyl) | 90 | 180 | hydro-chloride | 193 |
| 149 | N(CH₃)SO₂CH₃, HO—Ph—CH(OH)—CH₂—NH—C(CH₃)₂—(CH₂)₂—N(oxazolidinone-N-phenyl) | 72 | | hydro-chloride | 212 |
| 150 | N(CH₃)SO₂CH₃, HO—Ph—CH(OH)—CH₂—NH—(CH₂)₃—N(oxazolidinone-N-phenyl) | 69 | | hydro-chloride | 182 |
| 151 | CONHNH₂, HO—Ph—CH(OH)—CH₂—NH—C(CH₃)₂—(CH₂)₃—N(oxazolidinone-N-phenyl) | 76 | | hydro-chloride | 221 |

TABLE II-continued
| Ex. No. | Formula | Yield % of theory | m.p. of Base °C. | Salt | m.p. of Salt °C. |
|---|---|---|---|---|---|
| 152 | 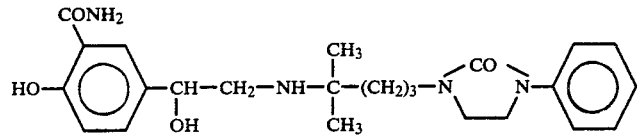 | 82 | 113 | hydro-chloride . H₂O | 80–82 |
| 153 | 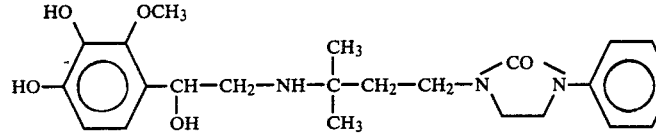 | 79 | | formate | 138 |
| 154 | 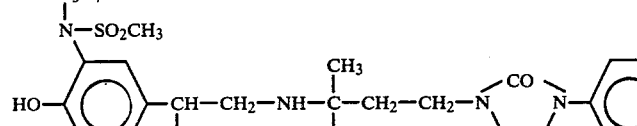 | 72 | | methane-sulfonate . H₂O | 120 |
| 155 | 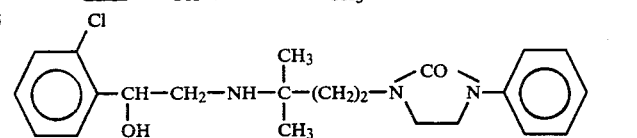 | 76 | | hydro-chloride | 252 |
| 156 | 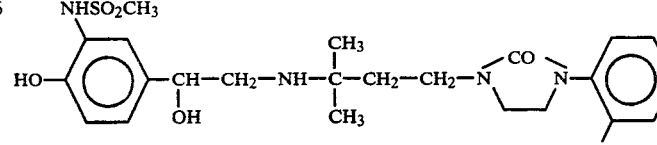 | 81 | | sulfate | 192 |
| 157 | 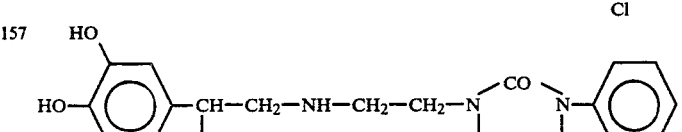 | 72 | | hydro-chloride | 209 |
| 158 | 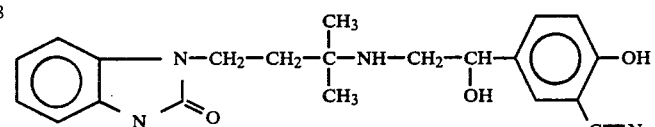 | | | hydro-chloride . H₂O | 173–176 |
| 159 | 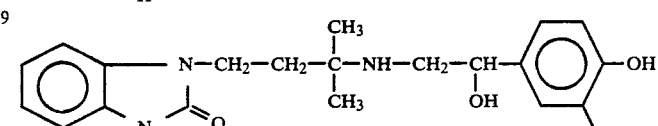 | 83 | | hydro-chloride | amor-phous |
| 160 | 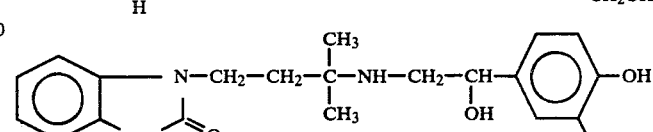 | 78 | 156 | hydro-chloride | 188 |
| 161 | 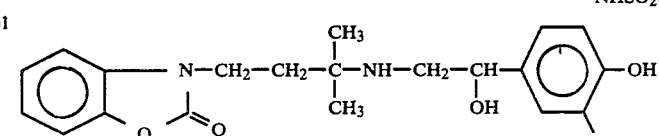 | 86 | | maleate | 176 |
| 162 | 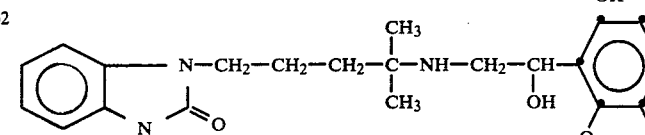 | 62 | | hydro-chloride | decomp. >230 |

TABLE II-continued
| Ex. No. | Formula | Yield % of theory | m.p. of Base °C. | Salt | m.p. of Salt °C. |
|---|---|---|---|---|---|
| 163 | 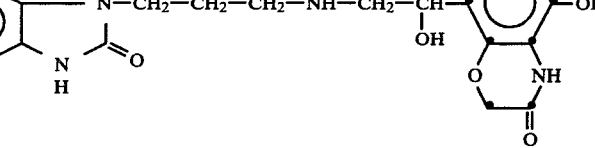 | 57 | | methane-sulfonate | decomp. >230 |
| 164 |  | 67 | | hydro-chloride | decomp. >220 |
| 165 | 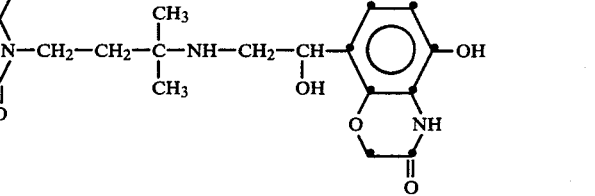 | 58 | | sulfate | decomp. >240 |
| 166 |  | 71 | | hydro-chloride | decomp. >230 |
| 167 | 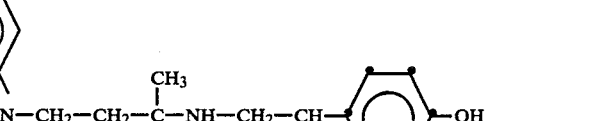 | 52 | | hydro-chloride | decomp. >230 |
| 168 | 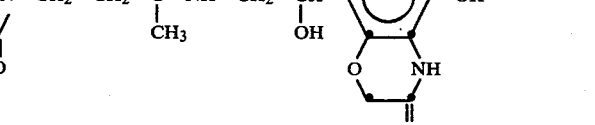 | 67 | | hydro-chloride | decomp. >220 |

TABLE II-continued

| Ex. No. | Formula | Yield % of theory | m.p. of Base °C. | Salt | m.p. of Salt °C. |
|---|---|---|---|---|---|
| 169 | | 82 | | methane-sulfonate | decomp. >240 |
| 170 | | | | hydro-chloride | decomp. >230 |
| 171 | | 61 | | hydro-chloride | decomp. >240 |
| 172 | | 69 | | hydro-chloride | decomp. >220 |

EXAMPLE 173

A solution of 9.1 gm of m-benzyloxy-ω-bromoacetophenone in 75 ml of ethanol was admixed at −5° C. with 1.2 gm of sodium borohydride, and the mixture was stirred for half an hour. The resulting solution was admixed with a little hydrobromic acid, the ethanol was distilled off under reduced pressure, and the residue was taken up in ethyl acetate. The solution was extracted first with an aqueous sodium bicarbonate solution and then with water, dried and evaporated in vacuo. The residue was taken up in 45 ml of dimethylformamide, admixed with 6.57 gm of 1-(4-amino-4,4-dimethylbutyl)-benzimidazolidinone-(2) and 6.65 gm of sodium carbonate, and the mixture was stirred for 6 hours at 105° C. After working up, the reaction product was isolated as its succinate of the formula

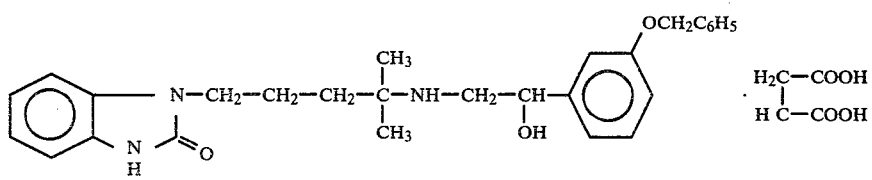

which had a melting point of 94° C. The yield was 58% of theory.

Using an analogous procedure and corresponding starting compounds, the compounds shown in the following table were also prepared:

Table III

| Ex. No. | Formula | Yield % of theory | m.p. of Base °C. | Salt | m.p. of Salt °C. |
|---|---|---|---|---|---|
| 174 | 3,4-Cl₂-C₆H₃-CH(OH)-CH₂-NH-C(CH₃)₂-(CH₂)₂-N(3-oxo-benzoxazine) | 61 | | p-amino-benzoate | 166 |
| 175 | 3-C₆H₅CH₂O-C₆H₄-CH(OH)-CH₂-NH-(CH₂)₃-N(2-oxo-tetrahydroquinoline) | 59 | 68 | | |
| 176 | 2-Cl-C₆H₄-CH(OH)-CH₂-NH-C(CH₃)₂-(CH₂)₂-N(benzimidazolone) | 62 | | maleate | 210 |
| 177 | 2-Cl-C₆H₄-CH(OH)-CH₂-NH-C(CH₃)₂-(CH₂)₃-N(benzimidazolone) | 68 | | hydrochloride | 239 |
| 178 | 2-Cl-C₆H₄-CH(OH)-CH₂-NH-C(CH₃)₂-(CH₂)₂-N(2-oxo-tetrahydroquinoline) | 76 | | p-aminobenzoate | 152.5 |
| 179 | 2-Cl-C₆H₄-CH(OH)-CH₂-NH-C(CH₃)₂-(CH₂)₂-N(3-oxo-benzoxazine) | 73 | | p-amino-benzoate | 159 |
| 180 | 3-C₆H₅CH₂O-C₆H₄-CH(OH)-CH₂-NH-C(CH₃)₂-(CH₂)₂-N(4-phenyl-2-oxopiperazine) | 64 | 122 | | |
| 181 | 2-Cl-C₆H₄-CH(OH)-CH₂-NH-C(CH₃)₂-(CH₂)₃-N(4-phenyl-2-oxopiperazine) | 64 | | sulfate | 225 |
| 182 | 2-naphthyl-CH(OH)-CH₂-NH-CH₂-CH₂-N(benzimidazolone) | 47 | 170 | methane-sulfonate | 185 |

EXAMPLE 183

By reacting 69.6 gm of the compound of the formula

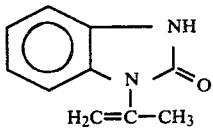

with 55.6 gm of chloroacetone in the presence of potassium carbonate and potassium iodide in acetone, followed by acid-catalyzed hydrolysis, 32 gm of the compound of the formula

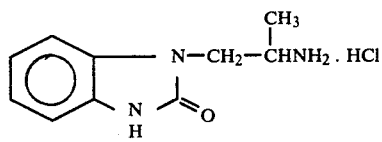

The yield was 15.6 gm.

EXAMPLE 184

A mixture consisting of 35 gm of 3,4-dibenzyloxy-ω-bromoacetophenone, 24 gm of 1-(3-benzylamino-n-propyl)-benzimidazolinone-(2), 22 gm of sodium carbonate and 300 ml of acetonitrile was refluxed for 2 hours. The reaction product of the formula

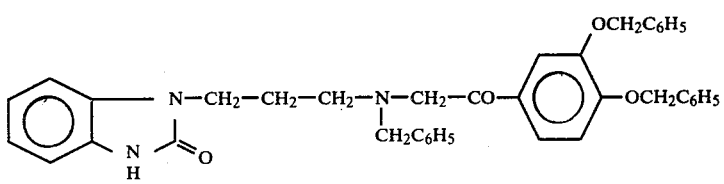

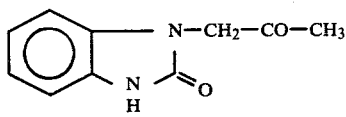

was isolated at its bioxalate with a yield of 44 gm (m.p. 168° C.). The free base (m.p. 112° C.) was liberated with aqueous ammonia. 35 gm of the base were dissolved in 350 ml of ethanol, 29 ml of 2 N sodium hydroxide were added to the solution, and then a total of 6 gm of sodium borohydride were added in portions over a period of 90 minutes. The reaction product of the formula

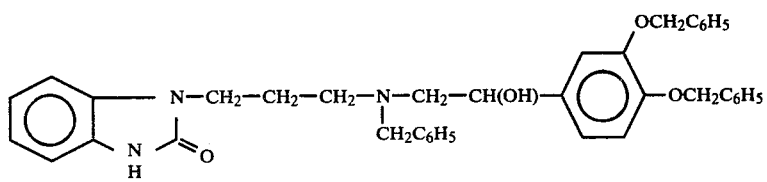

m.p. 182° C. were obtained. A solution of 19 gm of this substance in 300 ml of methanol was admixed with 25 ml of ammonia, and the mixture was hydrogenated with Raney nickel as the catalyst at 50° to 60° C. and 6 atmospheres. The hydrogenation product was isolated as its hydrochloride, m.p. 267°-270° C., of the formula was isolated as the free base (m.p. 93° C.).

A solution of 15 gm of the base in 150 ml of methanol was hydrogenated in the presence of 3 gm of palladized coal at 60° C. and 6 atmospheres until 3 molar equivalents of hydrogen had been absorbed. After removal of the catalyst, the solution was admixed with a solution of 2 gm of succinic acid in 20 ml of hot methanol, yielding 77% of theory of the crystalline succinate, m.p. 204° C., of the formula

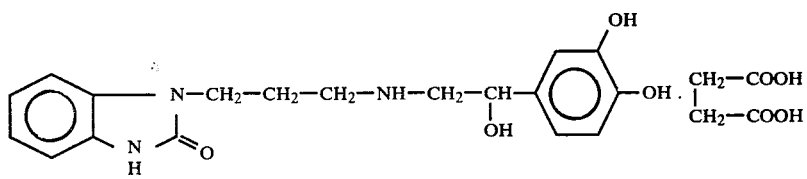

Using analogous procedures and starting compounds, the compounds shown in the following table were also prepared:

Table IV

| Ex. No. | Formula | Yield % of theory | m.p. of Base °C. | Salt | m.p. of Salt °C. |
|---|---|---|---|---|---|
| 185 | 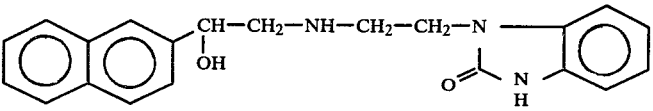 | 81 | 170 | methane-sulfonate | 185 |
| 186 | 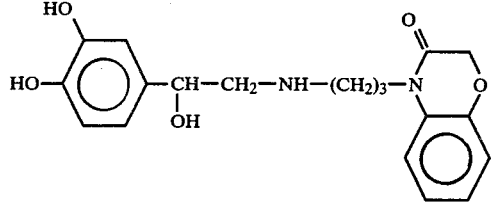 | 77 | | succinate | 189 |
| 187 | 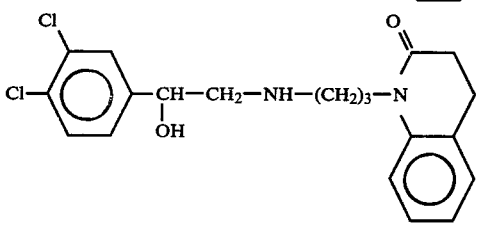 | 62 | | hydrochloride | 185 |
| 188 | 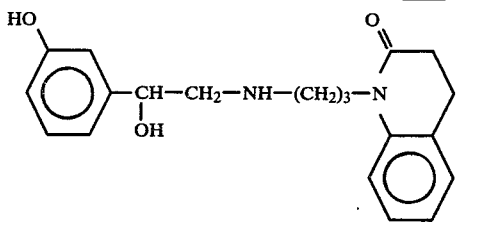 | 91 | | hydrochloride | 198 |
| 189 | 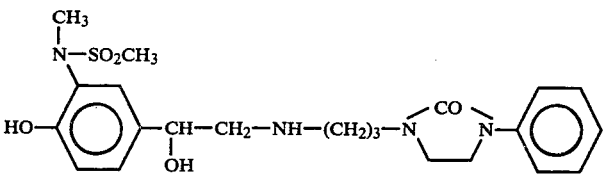 | 82 | | hydrochloride | 182 |

EXAMPLE 190

A solution of 7 gm of the compound of the formula

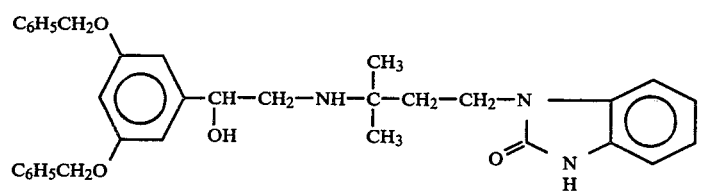

in 200 ml of methanol was hydrogenated in the presence of 1 gm of palladized coal under standard conditions until 2 molar equivalents of hydrogen had been absorbed. The hydrogenation product was isolated with a yield of 94% of theory as its maleate (m.p. 180° C., with 1 mol of water of crystallization) of the formula

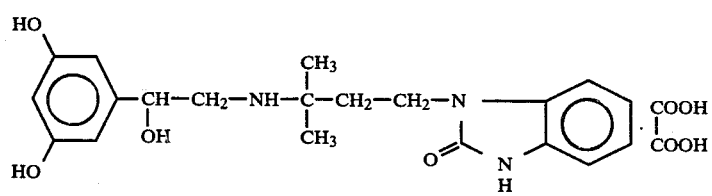

Using analogous procedures and starting compounds, the compounds shown in the following table were also prepared:

Table V
| Ex. No. | Formula | Yield % of theory | m.p. of Base °C. | Salt | m.p. of Salt °C. |
|---|---|---|---|---|---|
| 191 | 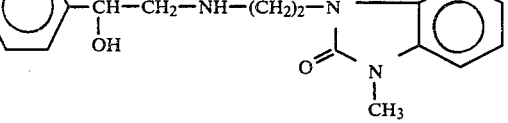 | 91 | | hydrochloride | 185 |
| 192 | 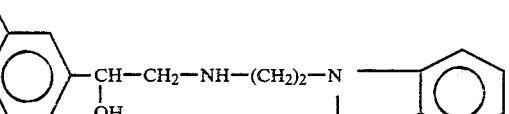 | 92 | | cyclamate | 176 |
| 193 | 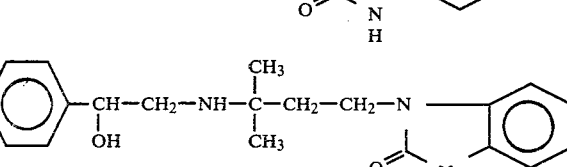 | 89 | | maleate | 134 |
| 194 | 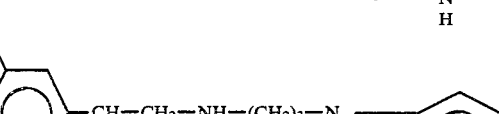 | 90 | | succinate | 204 |
| 195 | 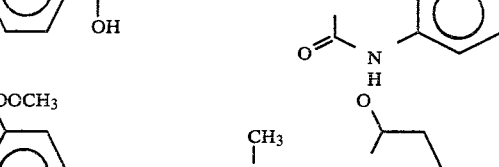 | 90 | | hydrochloride | 170 |
| 196 | 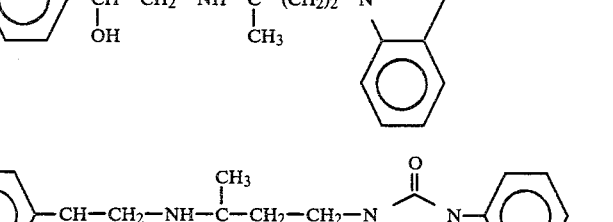 | 85 | | hydrochloride | 158 |
| 197 | 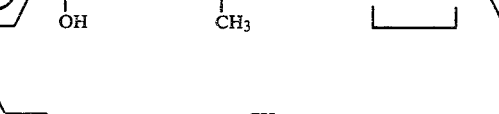 | 86 | | maleate | 168 |
| 198 | 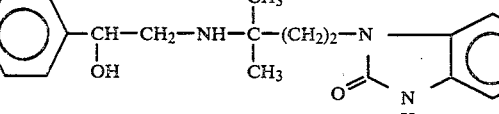 | 91 | | hydrochloride | 265 |
| 199 | 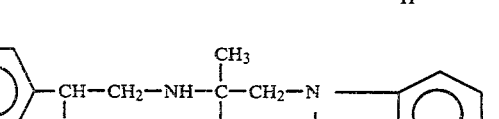 | 90 | | hydrochloride × 2 H$_2$O | 275 |

Table V-continued

| Ex. No. | Formula | Yield % of theory | m.p. of Base °C. | Salt | m.p. of Salt °C. |
|---|---|---|---|---|---|
| 200 | HO—C₆H₄—CH(OH)—CH₂—NH—C(CH₃)₂—(CH₂)₂—N(benzimidazolone-NH) | 85 | | maleate | 180 |
| 201 | (HO)(HO)(CH₃)C₆H₂—CH(OH)—CH₂—NH—C(CH₃)₂—(CH₂)₂—N(benzimidazolone-NH) | 91 | | maleate | 157 |
| 202 | (HO)(HO)C₆H₃—CH(OH)—CH₂—NH—C(CH₃)₂—(CH₂)₂—N(benzimidazolone-NH) | 94 | | maleate | 138 |
| 203 | (HO)(HO)(CH₃)C₆H₂—CH(OH)—CH₂—NH—C(CH₃)₂—CH₂—CH₂—N(benzimidazolone-N-CH₃) | 83 | | succinate | 176 |
| 204 | HO—C₆H₄—CH(OH)—CH₂—NH—C(CH₃)₂—(CH₂)₂—N(benzoxazinone) | 93 | | p-amino-benzoate | 193 |
| 205 | (HO)(HO)C₆H₃—CH(OH)—CH₂—NH—C(CH₃)₂—(CH₂)₂—N(benzoxazinone) | 92 | | succinate | 171 |
| 206 | HO—C₆H₄—CH(OH)—CH₂—NH—C(CH₃)₂—(CH₂)₃—N(benzimidazolone-NH) | 93 | | succinate × H₂O | 128 |
| 207 | (HO)(HO)C₆H₃—CH(OH)—CH₂—NH—C(CH₃)₂—(CH₂)₃—N(benzimidazolone-NH) | 92 | | succinate | 215 |

Table V-continued

| Ex. No. | Formula | Yield % of theory | m.p. of Base °C. | Salt | m.p. of Salt °C. |
|---|---|---|---|---|---|
| 208 | HNSO₂CH₃ / HO–C₆H₃–CH(OH)–CH₂–NH–C(CH₃)₂–(CH₂)₂–N(phenyl-NHC(=O)) | 90 | | hydrochloride | 177 |
| 209 | HO,HO–C₆H₃–CH(OH)–CH₂–NH–C(CH₃)₂–(CH₂)₂–N(3,4-dihydroquinolin-2(1H)-one) | 84 | | formate | 214 |
| 210 | CONH₂, HO–C₆H₃–CH(OH)–CH₂–NH–C(CH₃)₂–(CH₂)₂–N(3,4-dihydroquinolin-2(1H)-one) | 90 | 190 | hydrochloride | 225 |
| 211 | COOCH₃, HO–C₆H₃–CH(OH)–CH₂–NH–C(CH₃)₂–(CH₂)₂–N(3,4-dihydroquinolin-2(1H)-one) | 82 | | hydrochloride | 170 |
| 212 | NHSO₂CH₃, HO–C₆H₃–CH(OH)–CH₂–NH–C(CH₃)₂–CH₂–CH₂–N(3,4-dihydroquinolin-2(1H)-one) | 93 | 193 | hydrochloride | 196 |
| 213 | HO,HO–C₆H₃–CH(OH)–CH₂–NH–(CH₂)₃–N(3,4-dihydroquinolin-2(1H)-one) | 9 | | hydrochloride | 175 |
| 214 | HNSO₂CH₃, HO–C₆H₃–CH(OH)–CH₂–NH–C(CH₃)₂–CH₂–N(benzimidazol-2(3H)-one) | 94 | 206 | hydrochloride | 169 |
| 215 | HNSO₂CH₃, HO–C₆H₃–CH(OH)–CH₂–NH–C(CH₃)₂–CH₂–CH₂–N(1-methylbenzimidazol-2(3H)-one) | 91 | 200 | hydrochloride | 201 |

Table V-continued

| Ex. No. | Formula | Yield % of theory | m.p. of Base °C. | Salt | m.p. of Salt °C. |
|---|---|---|---|---|---|
| 216 | HO-C6H3(HNSO2CH3)-CH(OH)-CH2-NH-C(CH3)2-CH2-CH2-N(benzoxazinone) | 86 | 198 | hydrochloride | 157 |
| 217 | HO-C6H3(N(CH3)SO2CH3)-CH(OH)-CH2-NH-C(CH3)2-(CH2)2-N(benzimidazolone) | 84 | | acid maleate | 202 |
| 218 | H3C-C6H3(HO)-CH(OH)-CH2-NH-C(CH3)2-CH2-CH2-N(benzimidazolone) | 92 | | acid maleate | 180 |
| 219 | (HO)2-C6H3-CH(OH)-CH2-NH-C(CH3)2-CH2-CH2-N(N-methylbenzimidazolone) | 92 | 212 | p-amino-benzoate | 234 |
| 220 | HO-C6H4-CH(OH)-CH2-NH-C(CH3)2-CH2-CH2-N(N-methylbenzimidazolone) | 93 | 148 | p-amino-benzoate | 191 |
| 221 | (HO)2-C6H3-CH(OH)-CH2-NH-(CH2)3-N(N-methylbenzimidazolone) | 92 | | hydrochloride | 190 |
| 222 | (HO)2-C6H3-CH(OH)-CH2-NH-(CH2)3-N(benzoxazinone) | 86 | | succinate | 189 |
| 223 | HO-C6H2(CH3)(HO)-CH(OH)-CH2-NH-C(CH3)2-CH2-CH2-N(benzoxazinone) | 84 | | formate × ½ CH3CN | 159 |

Table V-continued

| Ex. No. | Formula | Yield % of theory | m.p. of Base °C. | Salt | m.p. of Salt °C. |
|---|---|---|---|---|---|
| 224 | HO-C6H4-CH(OH)-CH2-NH-(CH2)3-N-(3,4-dihydroquinolin-2(1H)-one) | 89 | | hydrochloride | 198 |
| 225 | 3,5-(HO)2-C6H3-CH(OH)-CH2-NH-(CH2)3-N-(3,4-dihydroquinolin-2(1H)-one) | 90 | | p-amino-benzoate | 199 |
| 226 | 3-Cl-4-HO-C6H3-CH(OH)-CH2-NH-C(CH3)2-CH2-CH2-N-(benzimidazol-2(3H)-one) | 81 | | acid maleate | 168 |
| 227 | 3-NHSO2CH3-4-HO-C6H3-CH(OH)-CH2-NH-(CH2)3-N-(6,8-dichloro-3,4-dihydroquinolin-2(1H)-one) | 81 | | hydrochloride | 230 |
| 228 | 3-CONH2-4-HO-C6H3-CH(OH)-CH2-NH-C(CH3)2-CH2-CH2-N-(benzimidazol-2(3H)-one) | 84 | | hydrochloride | 252 |
| 229 | 3-N(CH3)SO2-4-HO-C6H3-CH(OH)-CH2-NH-(CH2)3-N-(2H-1,4-benzoxazin-3(4H)-one) | 90 | | succinate | 173 |
| 230 | 3-CONH2-4-HO-C6H3-CH(OH)-CH2-NH-C(CH3)2-(CH2)2-N-(2H-1,4-benzoxazin-3(4H)-one) | 93 | 198 | hydrochloride | 235 |

Table V-continued

| Ex. No. | Formula | Yield % of theory | m.p. of Base °C. | Salt | m.p. of Salt °C. |
|---|---|---|---|---|---|
| 231 | [structure: 3-methylsulfonamido-4-hydroxyphenyl-CH(OH)-CH₂-NH-C(CH₃)₂-CH₂-CH₂-N(3-oxo-benzoxazine)] | 85 | | succinate | 212 |
| 232 | [structure: 3-(N-propyl-methylsulfonamido)-4-hydroxyphenyl-CH(OH)-CH₂-NH-C(CH₃)₂-CH₂-CH₂-NH-(2-benzimidazolinone phenyl)] | 82 | | succinate | 218 |
| 233 | [structure: 3-(N-methylcarbamoyl)-4-hydroxyphenyl-CH(OH)-CH₂-NH-C(CH₃)₂-(CH₂)₂-N(3-oxo-benzoxazine)] | 84 | 180 | hydrochloride | 190 |
| 234 | [structure: 3,4-dihydroxy-2-methylphenyl-CH(OH)-CH₂-NH-C(CH₃)₂-(CH₂)₃-NH-(benzimidazolinone phenyl)] | 81 | | p-amino-benzoate | 190 |
| 235 | [structure: 3,5-dihydroxyphenyl-CH(OH)-CH₂-NH-C(CH₃)₂-(CH₂)₂-N(imidazolidinone)-phenyl] | 82 | 180 | succinate | 203 |
| 236 | [structure: 3,5-dihydroxyphenyl-CH(OH)-CH₂-NH-C(CH₃)₂-CH₂-CH₂-N(imidazolidinone)-phenyl] | 89 | | p-amino-benzoate | 196 |
| 237 | [structure: 3-methylsulfonamido-4-hydroxyphenyl-CH(OH)-CH₂-NH-C(CH₃)₂-CH₂-CH₂-N(imidazolidinone)-phenyl] | 92 | 180 | hydrochloride | 193 |
| 238 | [structure: 3-(N-methyl-methylsulfonamido)-4-hydroxyphenyl-CH(OH)-CH₂-NH-C(CH₃)₂-(CH₂)₂-N(imidazolidinone)-phenyl] | 82 | | hydrochloride | 212 |
| 239 | [structure: 3-(N-methyl-methylsulfonamido)-4-hydroxyphenyl-CH(OH)-CH₂-NH-(CH₂)₃-N(imidazolidinone)-phenyl] | 79 | | hydrochloride | 182 |

Table V-continued

| Ex. No. | Formula | Yield % of theory | m.p. of Base °C. | Salt | m.p. of Salt °C. |
|---|---|---|---|---|---|
| 240 | [structure: 3-CONHNH₂, 4-OH phenyl-CH(OH)-CH₂-NH-C(CH₃)₂-(CH₂)₃-N(CO-N-phenyl) cyclic] | 79 | | hydrochloride | 221 |
| 241 | [structure: 3-CONH₂, 4-OH phenyl-CH(OH)-CH₂-NH-C(CH₃)₂-(CH₂)₃-N(CO-N-phenyl) cyclic] | 80 | 113 | hydrochloride × H₂O | 80–82 |
| 242 | [structure: HO, OCH₃, HO phenyl-CH(OH)-CH₂-NH-C(CH₃)₂-CH₂-CH₂-N(CO-N-phenyl) cyclic] | 75 | | formate | 138 |
| 243 | [structure: N(C₃H₇)(SO₂CH₃), HO phenyl-CH(OH)-CH₂-NH-C(CH₃)₂-CH₂-CH₂-N(CO-N-phenyl) cyclic] | 82 | | methane-sulfonate × H₂O | 120 |
| 244 | [structure: NHSO₂CH₃, HO phenyl-CH(OH)-CH₂-NH-C(CH₃)₂-CH₂-CH₂-N(CO-N-(2-Cl-phenyl)) cyclic] | 86 | | sulfate | 192 |
| 245 | [structure: 3-Cl-phenyl-N(CO)N-CH₂-CH₂-C(CH₃)₂-NH-CH₂-CH(OH)-phenyl(OH, NHSO₂CH₃)] | 88 | 173 | hydrochloride | 203 |
| 246 | [structure: 3,4-(CH₃O)₂-phenyl-N(CO)N-CH₂-CH₂-C(CH₃)₂-NH-CH₂-CH(OH)-phenyl(OH, NHSO₂CH₃)] | 73.6 | 175 | hydrochloride | 216 |
| 247 | [structure: 4-CH₃O-phenyl-N(CO)N-CH₂-CH₂-C(CH₃)₂-NH-CH₂-CH(OH)-phenyl(OH, NHSO₂CH₃)] | 63 | | hydrochloride | 181 |
| 248 | [structure: 4-H₂N-phenyl-N(CO)N-CH₂-CH₂-C(CH₃)₂-NH-CH₂-CH(OH)-phenyl(OH, NHSO₂CH₃)] | 74 | 169 | dihydro-chloride | 206 |

Table V-continued

| Ex. No. | Formula | Yield % of theory | m.p. of Base °C. | Salt | m.p. of Salt °C. |
|---|---|---|---|---|---|
| 249 | | 72 | | | |
| 250 | | 69 | | hydro-chloride | amor-phous |
| 251 | | 87 | 156 | hydro-chloride | 188 |
| 252 | | 75 | | maleate | 176 |
| 253 | | 74 | | hydro-chloride | decomp. >230 |
| 254 | | 92 | | methane-sulfonate | decomp. >230 |
| 255 | | 88 | | hydro-chloride | decomp. >220 |
| 256 | | 87 | | sulfate | decomp. >240 |

Table V-continued

| Ex. No. | Formula | Yield % of theory | m.p. of Base °C. | Salt | m.p. of Salt °C. |
|---|---|---|---|---|---|
| 257 | | 78 | | hydro-chloride | decomp. >230 |
| 258 | | 80 | | hydro-chloride | decomp. >230 |
| 259 | | 78 | | hydro-chloride | decomp. >220 |
| 260 | | 72 | | methane-sulfonate | decomp. >240 |
| 261 | | 81 | | hydro-chloride | decomp. >230 |
| 262 | | 69 | | | |

EXAMPLE 263

A mixture consisting of 3.9 gm of the compound of the formula

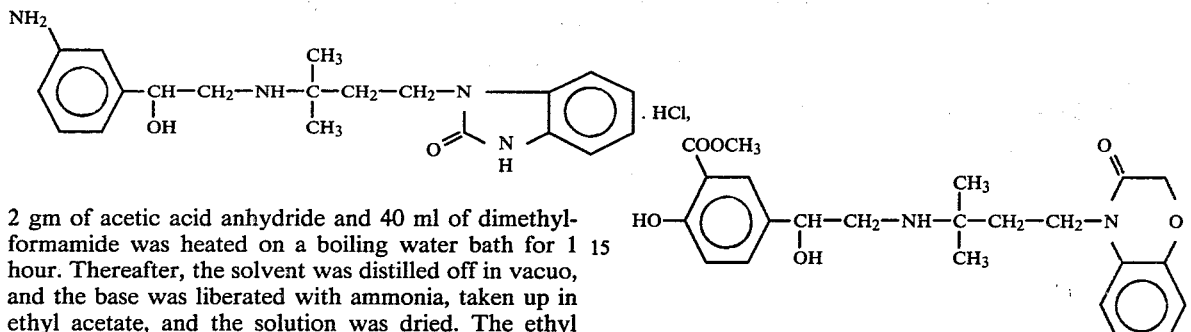

2 gm of acetic acid anhydride and 40 ml of dimethylformamide was heated on a boiling water bath for 1 hour. Thereafter, the solvent was distilled off in vacuo, and the base was liberated with ammonia, taken up in ethyl acetate, and the solution was dried. The ethyl acetate was distilled off, and the base was admixed in acetonitrile with the calculated amount of maleic acid, yielding 3.5 gm of the maleate of the formula

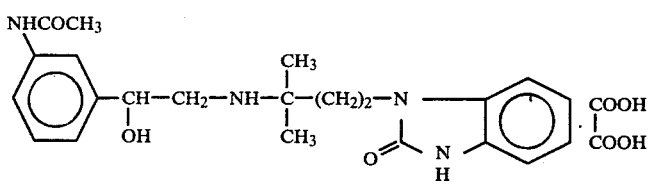

which had a melting point of 202° C. after recrystallization from methanol.

EXAMPLE 264

A solution of 6.1 gm of the compound of the formula

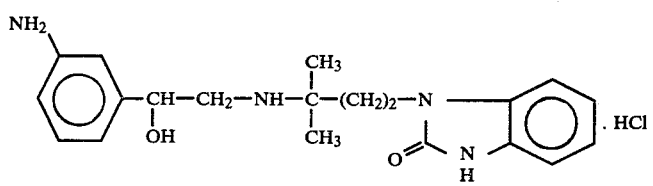

in a mixture of 20 ml of water and 7.5 ml of glacial acetic acid was admixed with a solution of 1.41 gm of potassium cyanate in 7.5 ml of water at 35° C. After standing overnight, the base was liberated with ammonia, separated by extracting it three times with isobutanol and converted into the maleate of the formula

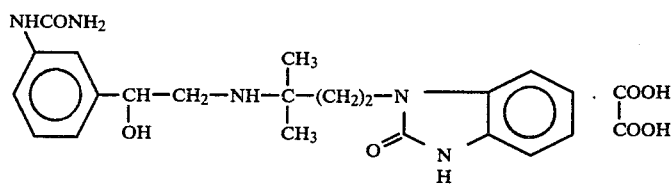

were obtained. After recrystallization from water, it had a melting point of 202° C.

EXAMPLE 265

A mixture consisting of 5 gm of the compound of the formula 100 ml of methanol and 100 ml of a concentrated aqueous ammonia solution was gently heated until a solution had formed. The solution was allowed to stand for an extended period of time, during which 4.3 gm of the base (m.p. 198° C.) of the formula

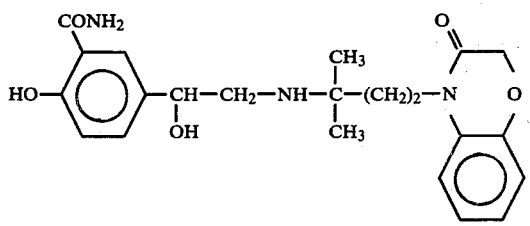

crystallized out. Its hydrochloride, obtained by acidifying an ethanolic solution of the base with hydrochloric acid, had a melting point of 235° C.

Using analogous procedures and corresponding starting compounds, the compounds shown in the following table were also prepared:

Table VI
| Ex. No. | Formula | Yield % of theory | m.p. of Base °C. | Salt | m.p. of Salt °C. |
|---|---|---|---|---|---|
| 266 | 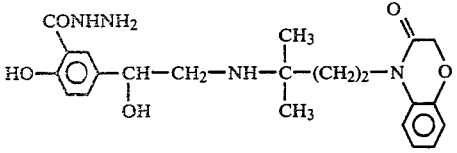 | 83 | 172 | hydrochloride | 204 |
| 267 | 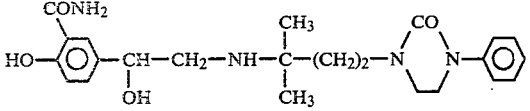 | 86 | 113 | hydrochloride x H₂O | 80–82 |
| 268 | 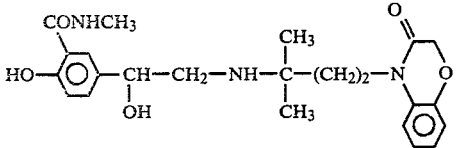 | 84 | 180 | hydrochloride | 190 |
| 269 | 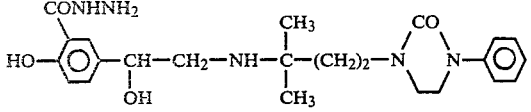 | 84 | | hydrochloride | 221 |
| 270 | 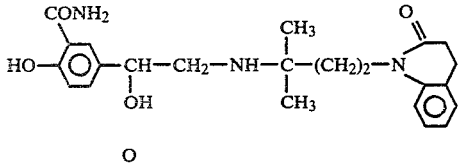 | 91 | 190 | hydrochloride | 225 |
| 271 | 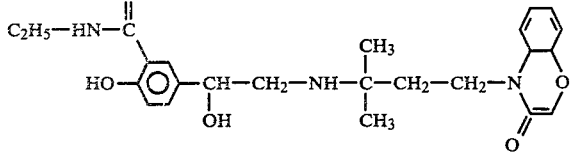 | 86 | | hydrochloride | 195 |
| 272 | 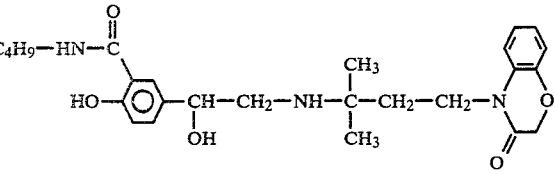 | 83.5 | | hydrochloride | 147 |
| 273 | 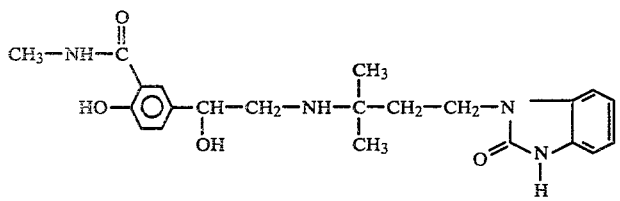 | 77 | | hydrochloride | 178 (decomp.) |
| 274 | 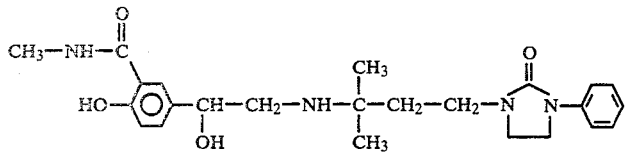 | 95 | | hydrochloride | 208 (decomp.) |
| 275 | 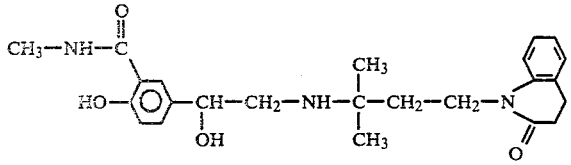 | 90 | 145 | hydrochloride | 215 (decomp.) |

Table VI-continued

| Ex. No. | Formula | Yield % of theory | m.p. of Base °C. | Salt | m.p. of Salt °C. |
|---|---|---|---|---|---|
| 276 | 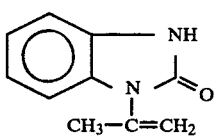 | 88 | | hydrochloride | 197 (decomp.) |
| 277 | 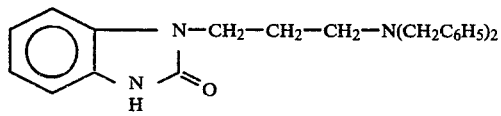 | 63 | 157 | hydro-chloride | 137 |

EXAMPLE 278

69.6 gm of the compound of the formula

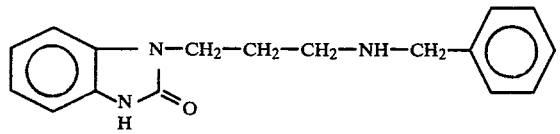

and then a solution of 0.44 mol of 3-(dibenzylamino)-n-propyl chloride in 300 ml of absolute ethanol were added to a solution of 0.42 mol of sodium in 200 ml of absolute ethanol, and the mixture was refluxed for six hours. Thereafter, the precipitated sodium chloride was separated, and the liquid phase was admixed with 45 ml of concentrated sulfuric acid while stirring and cooling. After three hours 700 ml of water were added, the ethanol was distilled off, and the residual solution was made alkaline with ammonia, whereupon the compound of the formula

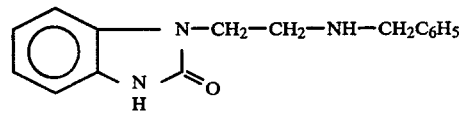

precipitated out. Recrystallized from acetonitrile, the product had a melting point of 146° C.

60 gm of this compound were hydrogenated in a mixture of 400 ml of methanol and 200 ml of water in the presence of 16 ml of concentrated hydrochloric acid and palladized coal at 60° C. and 6 atmospheres until 1 molar equivalent of hydrogen had been absorbed. 88% of theory of the compound of the formula

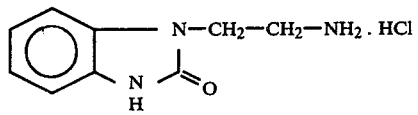

were obtained; it had a melting point of 60° C.

EXAMPLE 279

A solution of 53.4 gm of the compound of the formula

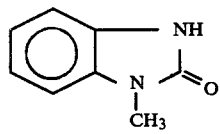

in 420 ml of methanol and 80 ml of water was hydrogenated in the presence of 20 ml of concentrated hydrochloric acid and palladized coal at 60° C. and 6 atmospheres until 1 molar equivalent of hydrogen had been absorbed. 91% of theory of the hydrochloride (m.p. 315° C.) of the formula $$\text{[structure]} \quad N-CH_2-CH_2-NH_2 \cdot HCl$$

was obtained.

EXAMPLE 280

10.1 gm of sodium hydride and 45 gm of N-(3-chloro-n-propyl)-phthalimide were added to a solution of 31.1 gm of the compound of the formula $$\text{[structure with NH, N-CH}_3\text{, C=O]}$$

in 150 ml of hexamethylphosphoric triamide (hexametapol) in an atmosphere of nitrogen, and the mixture was stirred for 5 hours at 100° C. The isolated raw reaction product of the formula

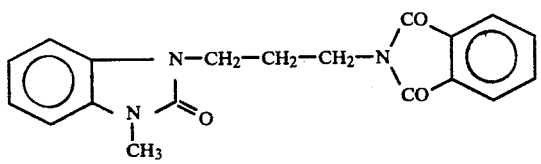

was refluxed in 1 liter of ethanol with 13 gm of 85% hydrazine hydrate for 90 minutes, admixed with 21 ml of concentrated hydrochloric acid and 100 ml of water, and heated again for 20 minutes. The precipitated phthalic acid hydrazide was separated by suction filtration, and the hydrochloride (m.p. 195° C. from ethanol) of the formula

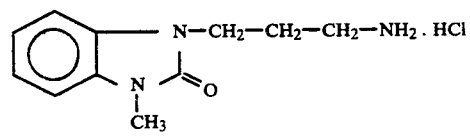

was isolated.

EXAMPLE 281

3.3 gm of sodium hydride (55%) were added to a solution of 9.2 gm of the compound of the formula

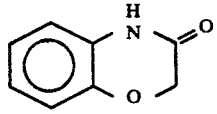

in 40 ml of absolute hexamethylphosphoric triamide in an atmosphere of nitrogen, and after the calculated amount of hydrogen had been released, a solution of 3-benzylamino-n-propyl chloride (b.p. 140° C. at 12 mm Hg) in 13 ml of hexamethylphosphoric triamide was added. The resulting mixture was stirred for 5 hours at 100° C., then poured over ice, and the reaction product of the formula

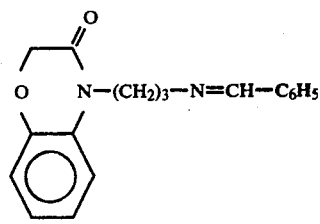

was isolated by extraction with ether and hydrolyzed without purification with 2 N hydrochloric acid, yielding 67% of theory of the hydrochloride of the formula

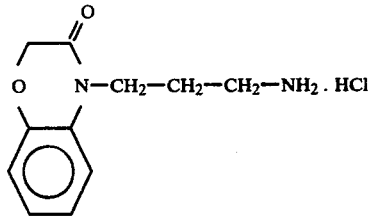

which had a melting point of 152°–155° C.

Using analogous procedures and corresponding starting compounds, the compounds shown in the following table were also prepared:

Table VII

| Ex. No. | Formula | Yield % of theory | m.p. of Base °C. | Salt | m.p. of Salt °C. |
|---|---|---|---|---|---|
| 282 | ![structure] | 84.5 | 175 | hydrochloride x H$_2$O | 280 |
| 283 | ![structure] | 54 | | hydrochloride | 150 |
| 284 | ![structure] | 62 | | maleate | 157 |

Table VII-continued

| Ex. No. | Formula | Yield % of theory | m.p. of Base °C. | Salt | m.p. of Salt °C. |
|---|---|---|---|---|---|
| 285 | [structure: dichlorophenyl with N-CH₂-CH₂-CH₂-NH₂ group] | 55 | | hydrochloride | 214-216 |
| 286 | [structure: benzimidazolinone with N-CH₂-CH₂-C(CH₃)₂-NH₂] | 90 | | hydrochloride | 277-79 |
| 287 | [structure: benzoxazinone with N-CH₂-CH₂-C(CH₃)₂-NH₂] | 68 | | hydrochloride | 237-239 |
| 288 | [structure: benzimidazolinone with N-(CH₂)₃-C(CH₃)₂-NH₂] | 75 | | hydrochloride | 266-268 |
| 289 | [structure: phenyl-N-CO-N cyclic with N-CH₂-CH₂-C(CH₃)₂-NH₂] | 74 | 76 | hydrochloride x H₂O | 140.5 |
| 290 | [structure: benzimidazolinone with N-CH₂-C(CH₃)₂-NH₂] | 92 | 135 | hydrochloride | 306 |
| 291 | [structure: benzimidazolinone with N-(CH₂)₃-NH₂] | 89 | | hydrochloride | 253 |
| 292 | [structure: chlorophenyl-N-CO-N cyclic with N-CH₂-CH₂-C(CH₃)₂-NH₂] | 65 | | p-amino-benzoate | 245 |
| 293 | [structure: dimethoxyphenyl-N-CO-N cyclic with N-CH₂-CH₂-C(CH₃)₂-NH₂] | 70 | | p-amino-benzoate | 225 |
| 294 | [structure: methylenedioxyphenyl-N-CO-N cyclic with N-CH₂-CH₂-C(CH₃)₂-NH₂] | 82 | | p-amino-benzoate | 233 |
| 295 | [structure: benzimidazolinone with N-CH(CH₃)-CH-NH₂] | 80 | | hydrochloride | 267-70 |

Table VII-continued

| Ex. No. | Formula | Yield % of theory | m.p. of Base °C. | Salt | m.p. of Salt °C. |
|---|---|---|---|---|---|
| 296 | ![structure] | 62 | | maleate | 179 |
| 297 | ![structure] | 87 | 81 | | |
| 298 | ![structure] | 75 | | hydrochloride | 246 |
| 299 | ![structure] | 72.3 | | hydrochloride | 185 |
| 300 | ![structure] | 61 | | hydrochloride | 225 |
| 301 | ![structure] | 60 | | hydrochloride | 202 |
| 302 | ![structure] | 89 | | hydrochloride | 225 |

EXAMPLE 303

A solution of 174 gm of the compound of the formula

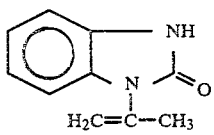

in 700 ml of absolute hexamethylphosphoric triamide was admixed with 48 gm of sodium hydride in the form of a 55% suspension, and after the evolution of hydrogen had ceased, a solution of 341 gm of the compound of the formula

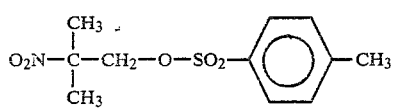

(m.p. 76° C.) in 450 ml of hexamethylphosphoric triamide was added. The mixed solution was stirred for 5 hours at 100° C., then poured over ice, extracted with ether, and after evaporation of the ether from the extract the residue was dissolved in 3 liters of ethanol, and the solution was admixed with 300 ml of 5 N sulfuric acid. The next day the reaction product of the formula

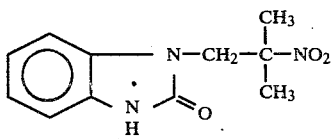

was isolated with a yield of 61% of theory (m.p. 198° C.). 58.75 gm of this compound were dissolved in 1700 ml of methanol, and after addition of Raney nickel the solution was hydrogenated at 6 atmospheres and 40°–60° C. The compound of the formula

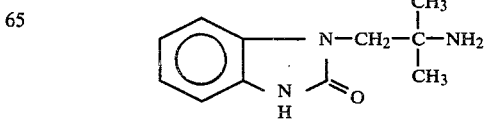

was isolated with a yield of 92% of theory (m.p. 135° C.). Its hydrochloride had a melting point of 306° C.

The compounds of the present invention, that is, those embraced by formula I above and their non-toxic, pharmacologically acceptable acid addition salts, have useful pharmacodynamic properties. More particularly, they exhibit coronary dilating and CNS-stimulating activities in warm-blooded animals, such as rats, guinea pigs and dogs, and are therefore useful as antihypertensives, bronchospasmolytics, circulation enhancers and antidepressants.

When R in formula I is a substituent group of the formula III, the nature of the variable substituents on the phenyl moiety thereof has an effect on the predominant pharmacological activity of these compounds.

For example, when $R_5$, $R_6$ and $R_7$ are lipophilic radicals or impart a lipophilic character to the substituent group of the formula III, the antidepressant activity predominates in these compounds. Such is the case, for instance, when $R_5$, $R_6$ and $R_7$ are hydrogen, halogen, alkoxy, amino, alkyl or trifluoromethyl, or when $R_7$ is hydrogen and $R_5$ and $R_6$ together with each other are ethylenedioxy or especially methylenedioxy.

When $R_5$, $R_6$ and $R_7$ are —$OR_8$ (where $R_8$ is hydrogen, acyl or aralkyl), —NH—acyl, amino or hydroxymethyl, or when $R_5$ and $R_6$ together with each other are —O—$CH_2$—CONH—, —$CH_2$— $CH_2$—CONH— or —O—CONH— and $R_7$ is hydroxyl, the vasodilating activity predominates in these compounds.

Finally, when $R_5$ is —$OR_8$ (where $R_8$ is hydrogen, acyl or aralkyl), $R_6$ is —$CONHR_3$ and $R_7$ is especially hydrogen, the antihypertensive activity predominates in these compounds.

Illustrative of the good pharmacological activity of the compounds of the present invention are the following data, where 22 times longer effective half-time and was 18 times more effective than the known vasodilator isoxsuprine.

Compound A, tested for antihypertensive activity on awake, genetically hypertonic rats, produced a decrease in blood pressure of 85 mm Hg at a dosage level of 30 mgm/kg i.p.

Compound C, tested for bronchospasmolytic activity in guinea pigs, was found to have a median effective dose $ED_{50}$ i.v. of 0.09 μgm/kg, whereas the corresponding $ED_{50}$-value for the known, highly effective bronchospasmolytic isoproterenol is 3.0 μgm/kg.

For pharmaceutical purposes the compounds according to the present invention are administered to warm-blooded animals perorally, parentereally, rectally or by the inhalation route as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories, inhalation sprays and the like. One effective dosage unit of the compounds according to the present invention is from 0.016 to 8.33 mgm/kg body weight, preferably 0.033 to 3.3 mgm/kg body weight, depending upon the form or mode of administration and the particular compound. The higher dosages are primarily adapted for sustained release compositions.

The following examples illustrate a few pharmaceutical dosage unit compositions comprising a compound of the present invention as an active ingredient and represent the best modes contemplated of putting the invention into practical use. The parts are parts by weight unless otherwise specified.

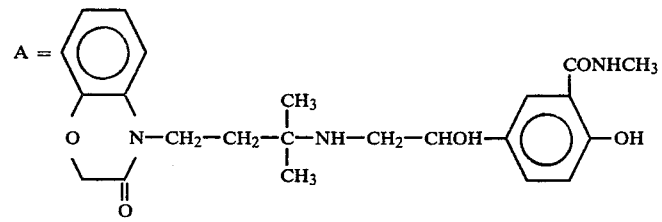

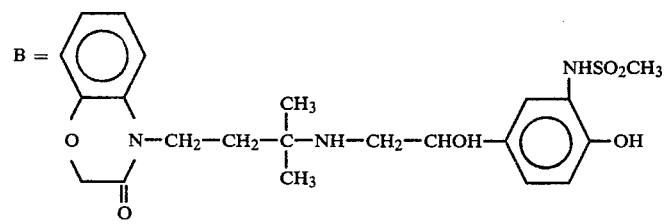

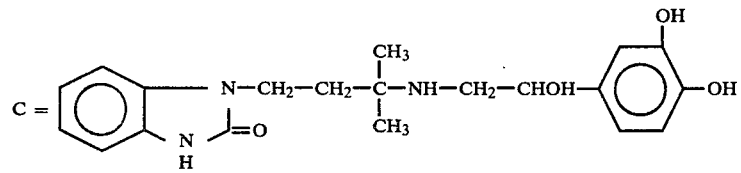

Compound B, tested for peripheral vasodilation in dogs by measurement of the blood flow through the left hind extremity after intra-arterial administration, had a

EXAMPLE 304

Tablets

The tablet composition is compounded from the following ingredients:

| | | |
|---|---|---|
| 1-(3,4-Methylenedioxy-phenyl)-2-[1,1-dimethyl-3-(benzimidazolidin-2-one-1-yl)-n-propyl-amino]-ethanol maleate (see Example 55) | | 2 parts |
| Stearic acid | | 6 parts |
| Glucose | | 592 parts |
| | Total | 600 parts |

Preparation

The ingredients are admixed in conventional manner, and the composition is compressed into 600 mgm-tablets. Each tablet contains 2 mgm of the active ingredient and is an oral dosage unit composition.

EXAMPLE 305

Suppositories

The suppository composition is compounded from the following ingredients:

| | | |
|---|---|---|
| 1-(3,4-Methylenedioxy-phenyl)-2-[1,1-dimethyl-3-(3-methylbenzimidazolidin-2-one-1-yl)-n-propyl-amino]-ethanol hydrochloride (see Example 63) | | 100 parts |
| Lactose, powdered | | 45 parts |
| Cocoa butter | | 1555 parts |
| | Total | 1700 parts |

Preparation

The ingredients are processed in conventional manner into 1700 mgm-suppositories, each of which contains 100 mgm of the active ingredient and is a rectal dosage unit composition.

EXAMPLE 306

Capsules

The capsule filler composition is compounded from the following ingredients:

| | | |
|---|---|---|
| 1-(3-Carboxymethylamido-4-hydroxyphenyl)-2-[1,1-dimethyl-3-(1,2,3,4-tetrahydro-quinol-2-one-1-yl)-n-propyl-amino]-ethanol hydrochloride (see Example 233) | | 200 parts |
| Lactose | | 440 parts |
| Corn starch | | 360 parts |
| | Total | 1000 parts |

Preparation

The ingredients are intimately admixed, the mixture is milled into a powder, and 1000 mgm-portions of the powder are filled into gelatin capsules of suitable size. Each capsule is an oral dosage unit composition containing 200 mgm of the active ingredient.

Any one of the other compounds embraced by formula I or a non-toxic, pharmacologically acceptable acid addition salt thereof may be substituted for the particular active ingredient in Examples 304 through 306. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic or optically active compound of the formula

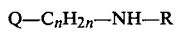

$$Q-C_nH_{2n}-NH-R$$

wherein Q is

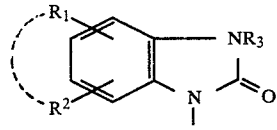

where $R_1$ is hydrogen, halogen, alkyl of 1 to 4 carbon atoms, alkoxy of 1 to 4 carbon atoms, trifluoromethyl or amino, $R_2$ is hydrogen, halogen, alkyl of 1 to 4 carbon atoms, alkoxy of 1 to 4 carbon atoms or trifluoromethyl, $R_1$ and $R_2$, together with each other, are methylenedioxy or ethylenedioxy, and n is an integer from 2 to 6, inclusive, and R is hydrogen, benzyl or

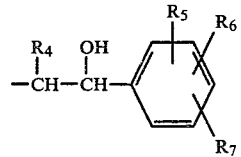

where $R_4$ is hydrogen, methyl or ethyl, $R_5$, $R_6$ and $R_7$, which may be identical to or different from each other, are each hydrogen, halogen, hydroxymethyl, trifluoromethyl, alkyl of 1 to 4 carbon atoms, alkoxy of 1 to 4 carbon atoms, nitro, cyano, —CONHR$_3$, —CONHOH, —COOR$_3$, R$_8$O—, methylsulfonylmethyl or, when one or two of the $R_5$ through $R_7$ are other than halogen or trifluoromethyl, also —NR$_3$R$_9$, where $R_3$ has the meanings defined above, $R_8$ is hydrogen, alkanoyl of 1 to 20 carbon atoms, alkyl of 1 to 4 carbon atoms or benzyl, and $R_9$ is hydrogen, lower alkanoyl, methanesulfonyl, carbamoyl, dimethylsulfamoyl, or alkoxycarbonyl of 2 to 5 carbon atoms, and $R_5$ and $R_6$, together with each other, are —O—CH$_2$—O—, —O—CH$_2$—CH$_2$—O—, —CH=CH—CH=CH—, —O—CH$_2$—CONH—, —CH$_2$—CH$_2$—CONH— or —O—CO—NH—, or a non-toxic, pharmacologically acceptable acid addition salt thereof.

2. A compound of claim 1, which is 1-(3,4-methylenedioxy-phenyl)-2-[1,1-dimethyl-3-(benzimidazolidin-2-one-1-yl)-n-propyl-amino]-ethanol or a non-toxic, pharmacologically acceptable acid addition salt thereof.

3. A compound of claim 1, which is 1-(3,4-methylenedioxy-phenyl)-2-[1,1-dimethyl-3-(3-methyl-benzimidazolidin-2-one-1-yl)-n-propyl-amino]-ethanol or a non-toxic, pharmacologically acceptable acid addition salt thereof.

4. A compound of claim 1, which is 1-(3-carboxymethylamido-4-hydroxy-phenyl)-2-[1,1-dimethyl-3-(3-methylbenzimidazolidin-2-one-1-yl)-n-propyl-amino]-ethanol or a non-toxic, pharmacologically acceptable acid addition salt thereof.

5. A vasodilating or antidepressant pharmaceutical dosage unit composition consisting essentially of an inert pharmaceutical carrier and an effective vasodilating or anti-depressant amount of a compound of claim 1.

6. The method of dilating the blood vessels or relieving depression in a warm-blooded animal in need thereof, which comprises perorally, parenterally or rectally administering to said animal an effective vasodilating or anti-depressant amount of a compound of claim 1.

* * * * *

UNITED STATES PATENT AND TRADEMARK OFFICE
CERTIFICATE OF CORRECTION

PATENT NO. : 4,215,119
DATED : July 29, 1980
INVENTOR(S) : ANTON MENTRUP ET AL.

It is certified that error appears in the above—identified patent and that said Letters Patent is hereby corrected as shown below:

Column 69, Example 260: The portion of the structural formula which reads

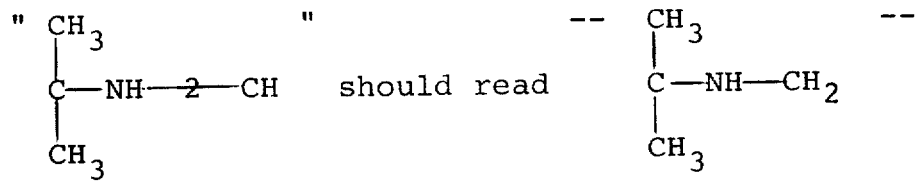

Column 75, Examples 276 and 277: The portion of the structural formula which reads

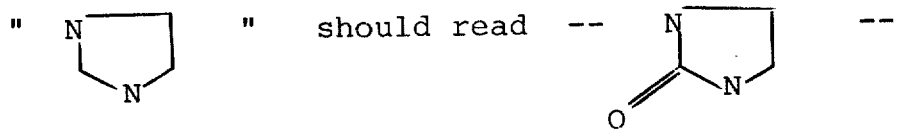

Signed and Sealed this

Twentieth Day of January 1981

[SEAL]

Attest:

RENE D. TEGTMEYER

Attesting Officer  Acting Commissioner of Patents and Trademarks

UNITED STATES PATENT AND TRADEMARK OFFICE
CERTIFICATE OF CORRECTION

PATENT NO. : 4,215,119
DATED : July 29, 1980
INVENTOR(S) : ANTON MENTRUP et al.

It is certified that error appears in the above-identified patent and that said Letters Patent is hereby corrected as shown below:

Column 86, between lines 28 and 29, should read as follows:

-- $R_3$ is hydrogen or alkyl of 1 to 4 carbon atoms, --

Signed and Sealed this

Eleventh Day of March 1986

[SEAL]

Attest:

DONALD J. QUIGG

Attesting Officer

Commissioner of Patents and Trademarks